US010105440B2

(12) United States Patent
Campbell

(10) Patent No.: US 10,105,440 B2
(45) Date of Patent: Oct. 23, 2018

(54) SYNTHETIC DERIVATIVES OF MPL AND USES THEREOF

(71) Applicant: VARIATION BIOTECHNOLOGIES INC., Ottawa (CA)

(72) Inventor: Maura Ellen Campbell, Greely (CA)

(73) Assignee: Variation Biotechnologies Inc., Ottawa (CA)

( * ) Notice: Subject to any disclaimer, the term of this patent is extended or adjusted under 35 U.S.C. 154(b) by 0 days.

(21) Appl. No.: 15/348,881

(22) Filed: Nov. 10, 2016

(65) Prior Publication Data

US 2017/0112924 A1    Apr. 27, 2017

Related U.S. Application Data

(62) Division of application No. 14/359,033, filed as application No. PCT/IB2012/002855 on Nov. 16, 2012.

(60) Provisional application No. 61/561,797, filed on Nov. 18, 2011.

(51) Int. Cl.

| | |
|---|---|
| A61K 39/39 | (2006.01) |
| A61K 39/00 | (2006.01) |
| C07H 13/04 | (2006.01) |
| C07H 13/06 | (2006.01) |
| A61K 39/145 | (2006.01) |
| A61K 39/112 | (2006.01) |
| A61K 39/02 | (2006.01) |
| A61K 39/21 | (2006.01) |
| A61K 39/29 | (2006.01) |
| C07H 15/12 | (2006.01) |
| A61K 39/12 | (2006.01) |
| A61K 9/00 | (2006.01) |
| A61K 9/127 | (2006.01) |
| A61K 9/19 | (2006.01) |

(52) U.S. Cl.
CPC ............ *A61K 39/39* (2013.01); *A61K 9/0019* (2013.01); *A61K 39/00* (2013.01); *A61K 39/0275* (2013.01); *A61K 39/099* (2013.01); *A61K 39/107* (2013.01); *A61K 39/12* (2013.01); *A61K 39/145* (2013.01); *A61K 39/21* (2013.01); *A61K 39/29* (2013.01); *A61K 39/292* (2013.01); *C07H 13/04* (2013.01); *C07H 13/06* (2013.01); *C07H 15/12* (2013.01); *A61K 9/127* (2013.01); *A61K 9/19* (2013.01); *A61K 2039/55555* (2013.01); *A61K 2039/55572* (2013.01); *C12N 2760/16034* (2013.01); *C12N 2760/16134* (2013.01); *C12N 2760/16234* (2013.01); *Y02A 50/484* (2018.01)

(58) Field of Classification Search
None
See application file for complete search history.

(56) References Cited

U.S. PATENT DOCUMENTS

| | | | |
|---|---|---|---|
| 5,858,368 | A | 1/1999 | Smith et al. |
| 5,919,480 | A | 7/1999 | Kedar et al. |
| 5,948,410 | A | 9/1999 | Van Scharrenburg et al. |
| 5,962,298 | A | 10/1999 | Fiers et al. |
| 6,136,606 | A | 10/2000 | Chatfield |
| 6,180,110 | B1 | 1/2001 | Funkhouser et al. |
| 6,287,570 | B1 | 9/2001 | Foley |
| 6,344,354 | B1 | 2/2002 | Webster et al. |
| 6,372,223 | B1 | 4/2002 | Kistner et al. |
| 6,534,065 | B1 | 3/2003 | Makin et al. |
| 6,605,457 | B1 | 8/2003 | Fiers et al. |
| 6,635,246 | B1 | 10/2003 | Barrett et al. |
| 6,740,325 | B1 | 5/2004 | Arnon et al. |
| 6,743,900 | B2 | 6/2004 | Burt et al. |
| 6,861,244 | B2 | 3/2005 | Barrett et al. |
| 6,991,929 | B1 | 1/2006 | D'Hondt |
| 7,052,701 | B2 | 5/2006 | Barrett et al. |
| 7,192,595 | B2 | 3/2007 | Arnon et al. |
| 7,244,435 | B2 | 7/2007 | Lai |
| 7,262,045 | B2 | 8/2007 | Trager et al. |
| 7,316,813 | B2 | 1/2008 | Eichhorn |
| 7,361,352 | B2 | 4/2008 | Birkett et al. |
| 7,399,840 | B2 | 7/2008 | Burt et al. |
| 7,468,259 | B2 | 12/2008 | Fiers et al. |
| 7,491,707 | B1 | 2/2009 | Jiang et al. |
| 7,494,659 | B2 | 2/2009 | Katinger et al. |
| 7,510,719 | B2 | 3/2009 | Dang et al. |
| 7,514,086 | B2 | 4/2009 | Arnon et al. |
| 7,527,800 | B2 | 5/2009 | Yang et al. |
| 7,537,768 | B2 | 5/2009 | Luke et al. |
| 9,610,248 | B2 * | 4/2017 | Anderson ............. A61K 9/127 |
| 2008/0131466 | A1 | 6/2008 | Reed et al. |
| 2009/0155309 | A1 | 6/2009 | Friede et al. |

(Continued)

FOREIGN PATENT DOCUMENTS

| | | |
|---|---|---|
| EP | 0413637 A1 | 2/1991 |
| WO | 2009029695 A1 | 3/2009 |
| WO | 2009155489 A2 | 12/2009 |

OTHER PUBLICATIONS

European Patent Application No. 12848780.8, European Office Action dated Aug. 2, 2017.
Advertising: Synthetic Adjuvant, Internet Citation, May 15, 2007 (May 15, 2007), pp. 1-6, XP002546530, ISSN: 0022-1767, Retrieved from the Internet, Sep. 17, 2009.
Andre et al., "Inactivated candidate vaccines for hepatitis A," Progresss in Medical Virology, 1990, vol. 37, pp. 72-95.
Avanti., "Advertising: The New Phad? In Vaccine Technology Avanti? Synthetic Vaccine Adjuvant", Internet Citation, Retrieved from the Internet: Dec. 15, 2007, pp. 1-6, XP002546531.
Collins et al., "Non-Ionic Surfactant Vesicle Formulation of Stibogluconate for Canine Leishmaniasis", Journal of Pharmacy and Pharmacology, Dec. 1990, vol. 42 (S1), p. 53. . . .

(Continued)

*Primary Examiner* — Stacy B Chen
(74) *Attorney, Agent, or Firm* — Borden Ladner Gervais LLP; David A. Nauman

(57) ABSTRACT

In one aspect, the present disclosure provides compounds of formulae I and II. In another aspect, a compound of formula I or II is formulated into compositions with an antigen, optionally with a vesicle. In some embodiments, compositions are administered intramuscularly.

19 Claims, 7 Drawing Sheets

(56) References Cited

U.S. PATENT DOCUMENTS

| | | |
|---|---|---|
| 2009/0181078 A1 | 7/2009 | Reed et al. |
| 2010/0310602 A1 | 12/2010 | Reed et al. |
| 2012/0156240 A1* | 6/2012 | Anderson ............ A61K 9/0019 424/204.1 |

OTHER PUBLICATIONS

Cregg et al., "High-Level Expression and Efficient Assembly of Hepatitis B Surface Antigen in the Methylotrophic Yeast, Pichia Pastoris", Biotechnology, May 1987, vol. 5, pp. 479-485.
European Patent Application No. 12848780, Supplementary European Search Report dated Apr. 13, 2015.
Fattovich, "Natural History of Hepatitis B," Journal of Hepatology, 39 (Suppl 1), vol. 2003, pp. S50-S58.
Fukuoka et al., "Structural Characterization of Lipid a Component of Erwinia Carotovora Lipopolysaccharide", Archives of Microbiology, Apr. 1992, vol. 157 (4), pp. 311-318.
Harford et al., "Expression of Hepatitis B Surface Antigen in Yeast," Developments in Biological Standardization, 1983, vol. 54, pp. 125-130.
Hilleman, "Critical Overview and Outlook: Pathogenesis, Prevention, and Treatment of Hepatitis and Hepatocarcinoma Caused by Hepatitis B Virus", Vaccine, Dec. 2003, vol. 21 (32), pp. 4626-4649.
International Patent Application No. PCT/IB2012/002855, International Preliminary Report on Patentability dated May 30, 2014.
International Patent Application No. PCT/IB2012/002855, International Search Report and Written Opinion dated Apr. 8, 2013.
Maeda et al., "Adjuvant Activities of Synthetic Lipid a Subunit Analogues and Its Conjugates With Muramyl Dipeptide Derivatives", Vaccine, Jun. 1989, vol. 7 (3), pp. 275-281.
Mao et al., "Further Evaluation of the Safety and Protective Efficacy of Live Attenuated Hepatitis a Vaccine (H2-strain) in Humans", Vaccine, Jun. 1997, vol. 15 (9), pp. 944-947.
McAleer et al., "Human Hepatitis B Vaccine from Recombinant Yeast", Nature, Jan. 1984, vol. 307 (5947), pp. 178-180.
Miller et al., "Hepatitis C Virus Shares Amino Acid Sequence Similarity with Pestiviruses and Flaviviruses as Well as Members of Two Plant Virus Supergroups", Proceedings of the National Academy of Sciences, Mar. 1990, vol. 87, pp. 2057-2061.
Provost et al., "New Findings in Live, Attenuated Hepatitis a Vaccine Development", Journal of Medical Virology, Oct. 1986, vol. 20 (2), pp. 165-175.
Ribi et al., "Modulation of Humoral and Cell-Mediated Immune Responses by a Structurally Established Nontoxic Lipid A," Immunology and Immunopharmacology of Bacterial Endotoxins, 1986, vol. 18, pp. 407-419.
Russell et al., "Effective Immunization Against Cutaneous Leishmaniasis With Defined Membrane Antigens Reconstituted Into Liposomes", Journal of Immunology, Feb. 1988, vol. 140 (4), pp. 1274-1279.
Ulrich et al., "The Adjuvant Activity of Monophosphoryl Lipid A", Topics in Vaccine Adjuvant Research, Dec. 19, 1991, pp. 133-145.
U.S. Appl. No. 14/359,033, Office Action dated May 13, 2016.
U.S. Appl. No. 14/359,033, Restriction Requirement dated Oct. 15, 2014.
Valenzuela et al., "Chemical Synthesis of a Gene for Human Epidermal Growth Factor Urogastrone and its Expression in Yeast", Proceedings of the National Academy of Sciences United States of America, Dec. 1983, vol. 80 (24), pp. 7461-7465.
Weiner et al., "Variable and Hypervariable Domains Are Found in the Regions of HCV Corresponding to the Flavivirus Envelope and NS1 Proteins and the Pestivirus Envelope Glycoproteins", Virology, Feb. 1991, vol. 180 (2), pp. 842-848.

* cited by examiner

SYNTHETIC DERIVATIVES OF MPL AND USES THEREOF

CROSS REFERENCE TO RELATED APPLICATIONS

This application is a divisional of U.S. application Ser. No. 14/359,033, which is a National Phase Entry of International Application No. PCT/IB2012/002855 filed Nov. 16, 2012, which claims priority to U.S. Provisional Application No. 61/561,797, filed Nov. 18, 2011, the contents of which are hereby incorporated by reference herein in their entirety.

BACKGROUND

Adjuvants are agents that enhance immune responses (e.g., see "Vaccine Design: The Subunit and Adjuvant Approach", *Pharmaceutical Biotechnology*, Volume 6, Eds. Powell and Newman, Plenum Press, New York and London, 1995). Adjuvants can be used in strategies for eliciting specific immune responses through the administration of vaccines.

Lipopolysaccharide (LPS) is a unique glycolipid found in the outer leaflet of the outer membrane of Gram-negative bacteria and has been shown to be a potent stimulator of the immune system. Unfortunately, its use in adjuvants has been curtailed by its toxic effects. A non-toxic derivative of LPS, monophosphoryl lipid A (MPL), produced by removal of the core carbohydrate group and the phosphate from the reducing-end glucosamine, has been described by Ribi et al (1986, Immunology and Immunopharmacology of Bacterial Endotoxins, Plenum Publ. Corp., NY, pp. 407-419). A further detoxified version of MPL results from the removal of the acyl chain from the 3-position of the disaccharide backbone, and is called 3-O-deacylated monophosphoryl lipid A (3D-MPL). Other MPL derivatives are described in U.S. Pat. No. 7,491,707 and U.S. Patent Publication Nos. 2008/0131466 and 2009/0181078. Despite these developments there remains a need in the art for new adjuvants including alternative chemically defined derivatives of MPL.

SUMMARY

In one aspect, the present disclosure provides compounds of formulae I and II. In another aspect, a compound of formula I or II is formulated into compositions with an antigen, optionally with a vesicle. In some embodiments, compositions are administered intramuscularly.

DEFINITIONS

Figure 1:
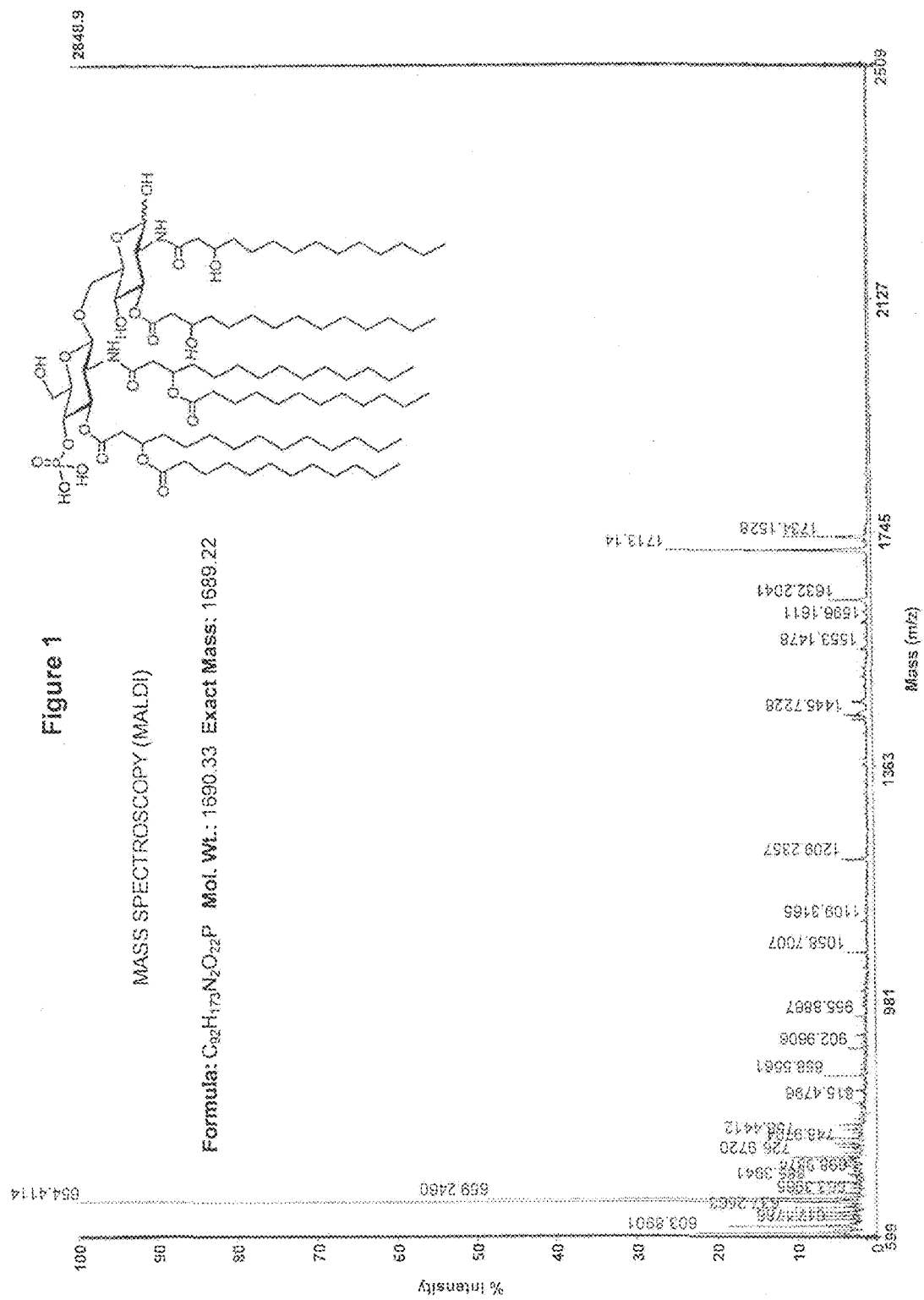
FIG. 1 is a MALDI-MS spectrum of compound 49 (also called "MAV4" herein).

Throughout the present disclosure, several terms are employed that are defined in the following paragraphs.

As used herein, the term "adjuvant" refers to a substance that enhances the ability of an antigen to stimulate the immune system.

As used herein, the term "alkyl" refers to saturated, straight- or branched-chain hydrocarbon radicals derived from an aliphatic moiety by removal of a single hydrogen atom. Examples of $C_8$-$C_{11}$ alkyl radicals include, but are not limited to, n-octyl, n-nonyl, n-decyl, n-undecyl, and the like.

As used herein, the term "antigen" refers to a substance containing one or more epitopes (either linear, conformational or both) that can be recognized by an antibody. In certain embodiments, an antigen can be a virus, a polypeptide, a polynucleotide, a polysaccharide, etc. The term "antigen" denotes both subunit antigens (i.e., antigens which are separate and discrete from a whole organism with which the antigen is associated in nature), as well as, killed, attenuated or inactivated bacteria, viruses, fungi, parasites or other microbes. In certain embodiments, an antigen may also be an "immunogen."

As used herein, the term "entrapped" refers to any kind of physical association between a substance and a vesicle, e.g., encapsulation, adhesion (to the inner or outer wall of the vesicle) or embedding in the wall with or without extrusion of the substance.

As used herein, the term "immune response" refers to a response elicited in an animal. An immune response may refer to cellular immunity, humoral immunity or may involve both. An immune response may also be limited to a part of the immune system. For example, in certain embodiments, an immunogenic composition may induce an increased IFNγ response. In certain embodiments, an immunogenic composition may induce a mucosal IgA response (e.g., as measured in nasal and/or rectal washes). In certain embodiments, an immunogenic composition may induce a systemic IgG response (e.g., as measured in serum). In certain embodiments, an immunogenic composition may induce virus-neutralizing antibodies or a neutralizing antibody response.

As used herein, the term "immunogenic" means capable of producing an immune response in a host animal against a non-host entity. In certain embodiments, this immune response forms the basis of the protective immunity elicited by a vaccine against a specific infectious organism. An "immunogen" is an immunogenic substance.

As used herein, the term "therapeutically effective amount" refers to the amount sufficient to show a meaningful benefit in a patient being treated. The therapeutically effective amount of an immunogenic composition may vary depending on such factors as the desired biological endpoint, the nature of the composition, the route of administration, the health, size and/or age of the patient being treated, etc.

As used herein, the term "polypeptide" refers to a protein (i.e., a string of at least two amino acids linked to one another by peptide bonds). In some embodiments, polypeptides may include moieties other than amino acids (e.g., may be glycoproteins, proteoglycans, lipoproteins, etc.) and/or may be otherwise processed or modified. Those of ordinary skill in the art will appreciate that a "protein" can be a complete polypeptide chain as produced by a cell (with or without a signal sequence), or can be a portion thereof. Those of ordinary skill will also appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, etc. In some embodiments, polypeptides may comprise natural amino acids, non-natural amino acids, synthetic amino acids, and combinations thereof.

As used herein, the term "polysaccharide" refers to a polymer of sugars. The polymer may include natural sugars (e.g., arabinose, lyxose, ribose, xylose, ribulose, xylulose, allose, altrose, galactose, glucose, gulose, idose, mannose, talose, fructose, psicose, sorbose, tagatose, mannoheptulose, sedoheptulose, octolose, and sialose) and/or modified sugars (e.g., 2'-fluororibose, 2'-deoxyribose, and hexose). Exemplary polysaccharides include starch, glycogen, dextran, cellulose, etc.

As used herein, the term "polynucleotide" refers to a polymer of nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, 4-acetylcytidine, 5-(carboxyhydroxymethyl)uridine, dihydrouridine, methylpseudouridine, 1-methyl adenosine, 1-methyl guanosine, N6-methyl adenosine, and 2-thiocytidine), chemically modified bases, biologically modified bases (e.g., methylated bases), intercalated bases, modified sugars (e.g., 2'-fluororibose, ribose, 2'-deoxyribose, 2'-O-methylcytidine, arabinose, and hexose), or modified phosphate groups (e.g., phosphorothioates and 5'-N-phosphoramidite linkages).

As used herein, the term "treat" (or "treating", "treated", "treatment", etc.) refers to the administration of a composition to a patient who has a disease, a symptom of a disease or a predisposition toward a disease, with the purpose to alleviate, relieve, alter, ameliorate, improve or affect the disease, a symptom or symptoms of the disease, or the predisposition toward the disease. In certain embodiments, the term "treating" refers to the vaccination of a patient.

DETAILED DESCRIPTION OF SOME EMBODIMENTS

In one aspect, the present disclosure provides compounds of formulae I and II. In another aspect, a compound of formula I or II is formulated into compositions with an antigen, optionally with a vesicle. In some embodiments, compositions are administered intramuscularly.

I. Compounds

In one aspect, the present disclosure provides compounds of formula I:

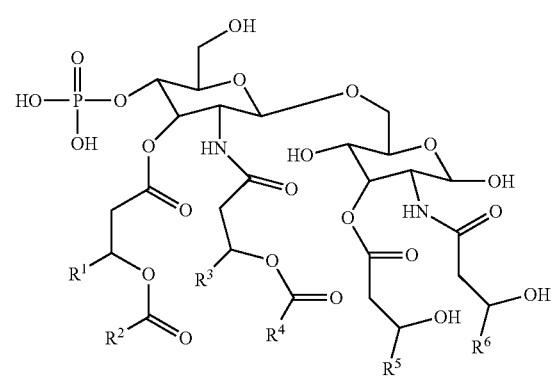

wherein:
$R^1$, $R^2$, $R^3$, $R^4$, $R^5$, and $R^6$ are independently selected from $C_x$ alkyl or $C_{x+1}$ alkyl; and
x is an integer from 6 to 20.

In certain embodiments, a compound of formula I is an adjuvant.

As defined generally above, $R^1$, $R^2$, $R^3$, $R^4$, $R^5$, and $R^6$ are independently selected from $C_x$ alkyl or $C_{x+1}$ alkyl. In some embodiments, $R^1$, $R^2$, $R^3$, $R^4$, $R^5$, and $R^6$ are the same. In some embodiments, $R^1$, $R^3$, $R^5$, and $R^6$ are the same. In some embodiments, $R^2$ and $R^4$ are the same. In some embodiments, $R^1$, $R^3$, $R^5$, and $R^6$ are $C_x$ alkyl, and $R^2$ and $R^4$ are $C_{x+1}$ alkyl. In some embodiments, $R^1$, $R^3$, $R^5$, and $R^6$ are $C_{x+1}$ alkyl, and $R^2$ and $R^4$ are $C_x$ alkyl.

As defined generally above, x is an integer from 6 to 20. In some embodiments, x is 6, 7, 8, 9, 10, or 11. In some embodiments, x is 6. In some embodiments, x is 8. In some embodiments, x is 11.

In some embodiments, $R^1$ is straight-chain alkyl. In some embodiments, $R^1$ is branched alkyl. In some embodiments, $R^2$ is straight-chain alkyl. In some embodiments, $R^2$ is branched alkyl. In some embodiments, $R^3$ is straight-chain alkyl. In some embodiments, $R^3$ is branched alkyl. In some embodiments, $R^4$ is straight-chain alkyl. In some embodiments, $R^4$ is branched alkyl. In some embodiments, $R^5$ is straight-chain alkyl. In some embodiments, $R^5$ is branched alkyl. In some embodiments, $R^6$ is straight-chain alkyl. In some embodiments, $R^6$ is branched alkyl.

In some embodiments, $R^1$, $R^2$, $R^3$, $R^4$, $R^5$, and $R^6$ are $C_6$ alkyl. In some embodiments, $R^1$, $R^2$, $R^3$, $R^4$, $R^5$, and $R^6$ are n-hexyl. In some embodiments, $R^1$, $R^2$, $R^3$, $R^4$, $R^5$, and $R^6$ are $C_8$ alkyl. In some embodiments, $R^1$, $R^2$, $R^3$, $R^4$, $R^5$, and $R^6$ are n-octyl. In some embodiments, $R^1$, $R^2$, $R^3$, $R^4$, $R^5$, and $R^6$ are $C_{11}$ alkyl. In some embodiments, $R^1$, $R^2$, $R^3$, $R^4$, $R^5$, and $R^6$ are n-undecyl.

In certain embodiments, at least one of $R^1$, $R^2$, $R^3$, $R^4$, $R^5$, and $R^6$ is $C_{11}$ alkyl. In certain embodiments, at least two of $R^1$, $R^2$, $R^3$, $R^4$, $R^5$, and $R^6$ are $C_{11}$ alkyl. In certain embodiments, at least three of $R^1$, $R^2$, $R^3$, $R^4$, $R^5$, and $R^6$ are $C_{11}$ alkyl. In certain embodiments, at least four of $R^1$, $R^2$, $R^3$, $R^4$, $R^5$, and $R^6$ are $C_{11}$ alkyl. In certain embodiments, at least five of $R^1$, $R^2$, $R^3$, $R^4$, $R^5$, and $R^6$ are $C_{11}$ alkyl. In certain embodiments, $R^1$, $R^2$, $R^3$, $R^4$, $R^5$, and $R^6$ are each $C_{11}$ alkyl. In certain embodiments, $R^1$, $R^2$, $R^3$, $R^4$, $R^5$, and $R^6$ are each n-undecyl.

In certain embodiments, at least one of $R^1$, $R^2$, $R^3$, $R^4$, $R^5$, and $R^6$ is $C_{10}$ alkyl. In certain embodiments, at least two of $R^1$, $R^2$, $R^3$, $R^4$, $R^5$, and $R^6$ are $C_{10}$ alkyl. In certain embodiments, at least three of $R^1$, $R^2$, $R^3$, $R^4$, $R^5$, and $R^6$ are $C_{10}$ alkyl. In certain embodiments, at least four of $R^1$, $R^2$, $R^3$, $R^4$, $R^5$, and $R^6$ are $C_{10}$ alkyl. In certain embodiments, at least five of $R^1$, $R^2$, $R^3$, $R^4$, $R^5$, and $R^6$ are $C_{10}$ alkyl. In certain embodiments, $R^1$, $R^2$, $R^3$, $R^4$, $R^5$, and $R^6$ are each $C_{10}$ alkyl. In certain embodiments, $R^1$, $R^2$, $R^3$, $R^4$, $R^5$, and $R^6$ are each n-decyl.

In certain embodiments, at least one of $R^1$, $R^2$, $R^3$, $R^4$, $R^5$, and $R^6$ is $C_9$ alkyl. In certain embodiments, at least two of $R^1$, $R^2$, $R^3$, $R^4$, $R^5$, and $R^6$ are $C_9$ alkyl. In certain embodiments, at least three of $R^1$, $R^2$, $R^3$, $R^4$, $R^5$, and $R^6$ are $C_9$ alkyl. In certain embodiments, at least four of $R^1$, $R^2$, $R^3$, $R^4$, $R^5$, and $R^6$ are $C_9$ alkyl. In certain embodiments, at least five of $R^1$, $R^2$, $R^3$, $R^4$, $R^5$, and $R^6$ are $C_9$ alkyl. In certain embodiments, $R^1$, $R^2$, $R^3$, $R^4$, $R^5$, and $R^6$ are each $C_9$ alkyl. In certain embodiments, $R^1$, $R^2$, $R^3$, $R^4$, $R^5$, and $R^6$ are each n-nonyl.

In certain embodiments, at least one of $R^1$, $R^2$, $R^3$, $R^4$, $R^5$, and $R^6$ is $C_8$ alkyl. In certain embodiments, at least two of $R^1$, $R^2$, $R^3$, $R^4$, $R^5$, and $R^6$ are $C_8$ alkyl. In certain embodiments, at least three of $R^1$, $R^2$, $R^3$, $R^4$, $R^5$, and $R^6$ are $C_8$ alkyl. In certain embodiments, at least four of $R^1$, $R^2$, $R^3$, $R^4$, $R^5$, and $R^6$ are $C_8$ alkyl. In certain embodiments, at least five of $R^1$, $R^2$, $R^3$, $R^4$, $R^5$, and $R^6$ are $C_8$ alkyl. In certain embodiments, $R^1$, $R^2$, $R^3$, $R^4$, $R^5$, and $R^6$ are each $C_8$ alkyl. In certain embodiments, $R^1$, $R^2$, $R^3$, $R^4$, $R^5$, and $R^6$ are each n-octyl.

In certain embodiments, at least one of $R^1$, $R^2$, $R^3$, $R^4$, $R^5$, and $R^6$ is $C_7$ alkyl. In certain embodiments, at least two of $R^1$, $R^2$, $R^3$, $R^4$, $R^5$, and $R^6$ are $C_7$ alkyl. In certain embodiments, at least three of $R^1$, $R^2$, $R^3$, $R^4$, $R^5$, and $R^6$ are $C_7$ alkyl. In certain embodiments, at least four of $R^1$, $R^2$, $R^3$, $R^4$, $R^5$, and $R^6$ are $C_7$ alkyl. In certain embodiments, at least five of $R^1$, $R^2$, $R^3$, $R^4$, $R^5$, and $R^6$ are $C_7$ alkyl. In certain embodiments, $R^1$, $R^2$, $R^3$, $R^4$, $R^5$, and $R^6$ are each $C_7$ alkyl. In certain embodiments, $R^1$, $R^2$, $R^3$, $R^4$, $R^5$, and $R^6$ are each n-heptyl.

In certain embodiments, at least one of $R^1$, $R^2$, $R^3$, $R^4$, $R^5$, and $R^6$ is $C_6$ alkyl. In certain embodiments, at least two of $R^1$, $R^2$, $R^3$, $R^4$, $R^5$, and $R^6$ are $C_6$ alkyl. In certain embodiments, at least three of $R^1$, $R^2$, $R^3$, $R^4$, $R^5$, and $R^6$ are $C_6$ alkyl. In certain embodiments, at least four of $R^1$, $R^2$, $R^3$, $R^4$, $R^5$, and $R^6$ are $C_6$ alkyl. In certain embodiments, at least five of $R^1$, $R^2$, $R^3$, $R^4$, $R^5$, and $R^6$ are $C_6$ alkyl. In certain embodiments, $R^1$, $R^2$, $R^3$, $R^4$, $R^5$, and $R^6$ are each $C_6$ alkyl. In certain embodiments, $R^1$, $R^2$, $R^3$, $R^4$, $R^5$, and $R^6$ are each n-hexyl.

In some embodiments, a compound of formula I is of formula I-a:

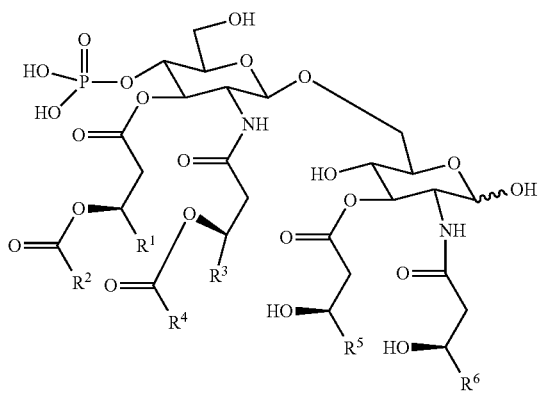

I-a wherein $R^1$, $R^2$, $R^3$, $R^4$, $R^5$, and $R^6$ are as defined and described herein.

In another aspect, the present disclosure provides compounds of formula II:

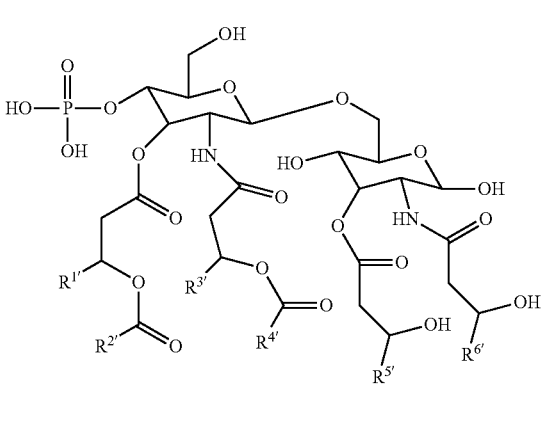

II wherein:

$R^{1'}$, $R^{3'}$, $R^{5'}$, and $R^{6'}$ are $C_y$ alkyl;

$R^{2'}$ and $R^{4'}$ are independently $C_y$ alkyl, $C_{y+1}$ alkyl, or $C_{y+2}$ alkyl; and y is 6 or 7.

In certain embodiments, a compound of formula II is an adjuvant.

As defined generally above, $R^{1'}$, $R^{3'}$, $R^{5'}$, and $R^{6'}$ are $C_y$ alkyl, and y is 6 or 7. In some embodiments, $R^{1'}$, $R^{3'}$, $R^{5'}$, and $R^{6'}$ are $C_6$ alkyl. In some embodiments, $R^{1'}$, $R^{3'}$, $R^{5'}$, and $R^{6'}$ are $C_7$ alkyl. In some embodiments, $R^{1'}$, $R^{3'}$, $R^{5'}$, and $R^{6'}$ are n-hexyl. In some embodiments, $R^{1'}$, $R^{3'}$, $R^{5'}$, and $R^{6'}$ are n-heptyl.

As defined generally above, $R^{2'}$ and $R^{4'}$ are $C_y$ alkyl, $C_{y+1}$ alkyl, or $C_{y+2}$ alkyl. In some embodiments, $R^{2'}$ and $R^{4'}$ are $C_y$ alkyl. In some embodiments, $R^{2'}$ and $R^{4'}$ are $C_{y+1}$ alkyl. In some embodiments, $R^{2'}$ and $R^{4'}$ are $C_{y+2}$ alkyl. In some embodiments, $R^{2'}$ is $C_y$ alkyl and $R^{4'}$ is $C_{y+1}$ alkyl. In some embodiments, $R^{2'}$ is $C_y$ alkyl and $R^{4'}$ is $C_{y+2}$ alkyl. In some embodiments, $R^{2'}$ is $C_{y+1}$ alkyl and $R^{4'}$ is $C_{y+2}$ alkyl. In some embodiments, $R^{2'}$ is $C_{y+1}$ alkyl and $R^{4'}$ is $C_y$ alkyl. In some embodiments, $R^{2'}$ is $C_{y+2}$ alkyl and $R^{4'}$ is $C_{y+1}$ alkyl. In some embodiments, $R^{2'}$ is $C_{y+2}$ alkyl and $R^{4'}$ is $C_y$ alkyl.

In some embodiments, $R^{2'}$ and $R^{4'}$ are $C_6$ alkyl. In some embodiments, $R^{2'}$ and $R^{4'}$ are n-hexyl. In some embodiments, $R^{2'}$ and $R^{4'}$ are $C_7$ alkyl. In some embodiments, $R^{2'}$ and $R^{4'}$ are n-heptyl. In some embodiments, $R^{2'}$ and $R^{4'}$ are $C_8$ alkyl. In some embodiments, $R^{2'}$ and $R^{4'}$ are n-octyl. In some embodiments, $R^{2'}$ and $R^{4'}$ are $C_9$ alkyl. In some embodiments, $R^{2'}$ and $R^{4'}$ are n-nonyl.

In some embodiments, a compound of formula II is of formula II-a:

II-a

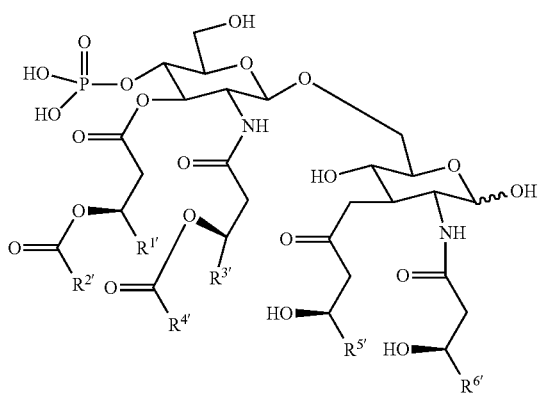

wherein $R^{1'}$, $R^{3'}$, $R^{4'}$, $R^{5'}$, and $R^{6'}$ are as defined and described herein.

An exemplary synthesis of a compound of formula I follows. One of ordinary skill in the art will appreciate that the same methods can be applied to synthesize a compound of formula II. One of ordinary skill in the art will also appreciate that, while the synthesis below shows intermediates of a particular stereochemistry, the methods described can be used to synthesize compounds having any desired stereochemistry or racemic compounds.

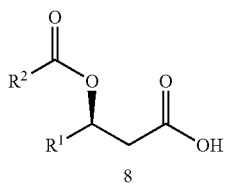

Scheme 1 depicts an exemplary synthesis of intermediate 8. In step 1-A, lactone 1 is ring-opened to give intermediate 2. In certain embodiments, step 1-A employs trimethylsilyl iodide. In step 1-B, intermediate 2 is cyclized to give epoxide 3. In certain embodiments, step 1-B employs silver (I) oxide. In step 1-C, epoxide 3 is allowed to react with an appropriate alkyl copper Grignard reagent to give intermediate 4. In step 1-D, the ester group of intermediate 4 is hydrolyzed to give intermediate 5. In step 1-E, the carboxylic acid group of intermediate 5 is protected as a phenacyl ester to give intermediate 6. One of ordinary skill in the art will appreciate that other protecting groups could be employed at step 1-E. In step 1-F, intermediate 6 is acylated to form intermediate 7, which is then deprotected in step 1-G to form intermediate 8. In certain embodiments, step 1-F employs an acyl chloride. In certain embodiments, step 1-F employs an anhydride. One of ordinary skill in the art will appreciate that Scheme 1 could also be employed to synthesize the analogous intermediate 9 having $R^3$ and $R^4$ groups:

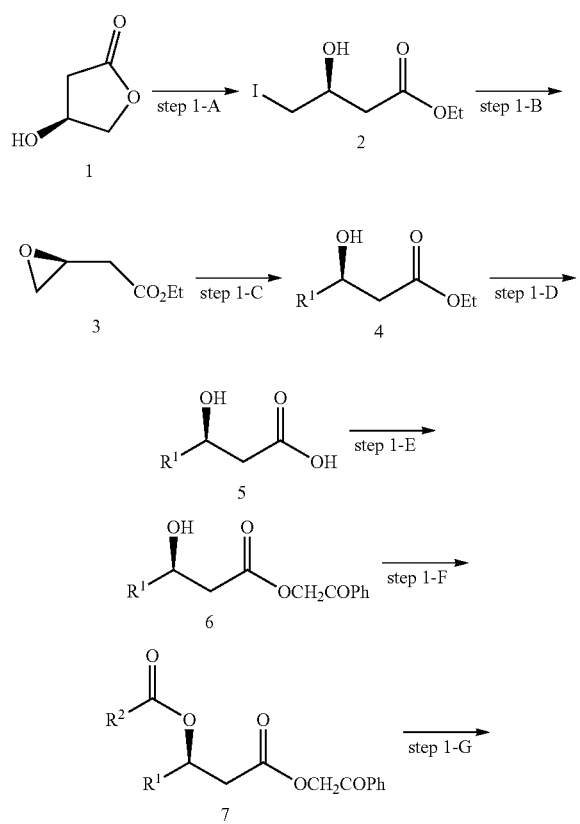

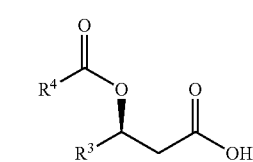

Scheme 2 depicts an exemplary synthesis of intermediate 12. Intermediate 10 is synthesized as described in Scheme 1, in an analogous manner to intermediate 6. In step 2-A, intermediate 10 is protected with a benzyl group. One of ordinary skill in the art will appreciate that other protecting groups may be used instead of benzyl in step 2-A. In step 2-B, the ester group of intermediate 11 is deprotected to give free acid intermediate 12. One of ordinary skill in the art will appreciate that Scheme 2 could also be employed to synthesize the analogous intermediate 13 having an $R^6$ group:

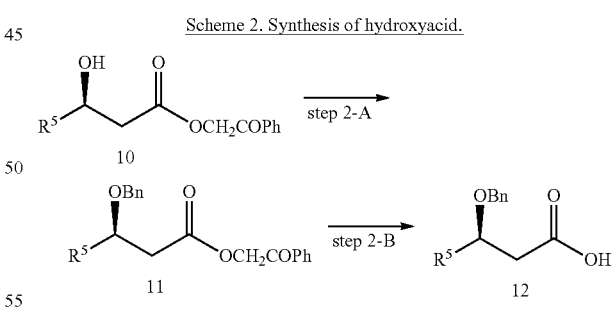

Scheme 3. Synthesis of glycosyl donor.

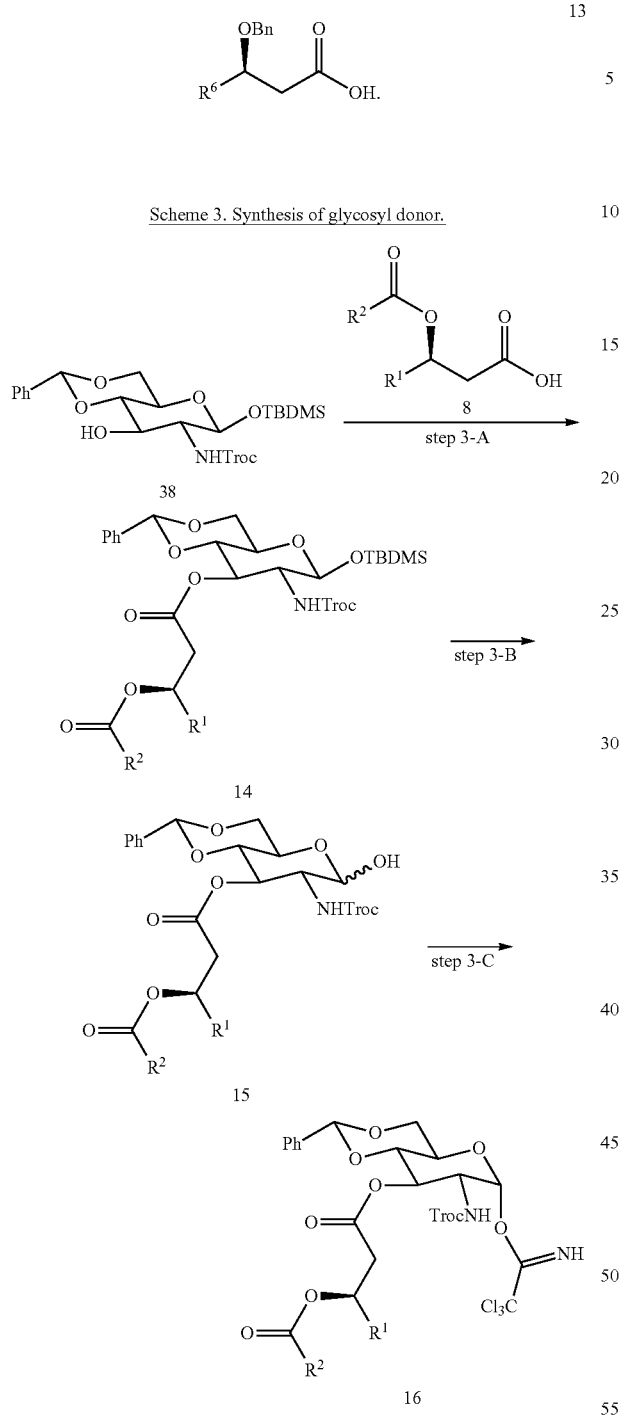

Scheme 4. Synthesis of glycosyl acceptor.

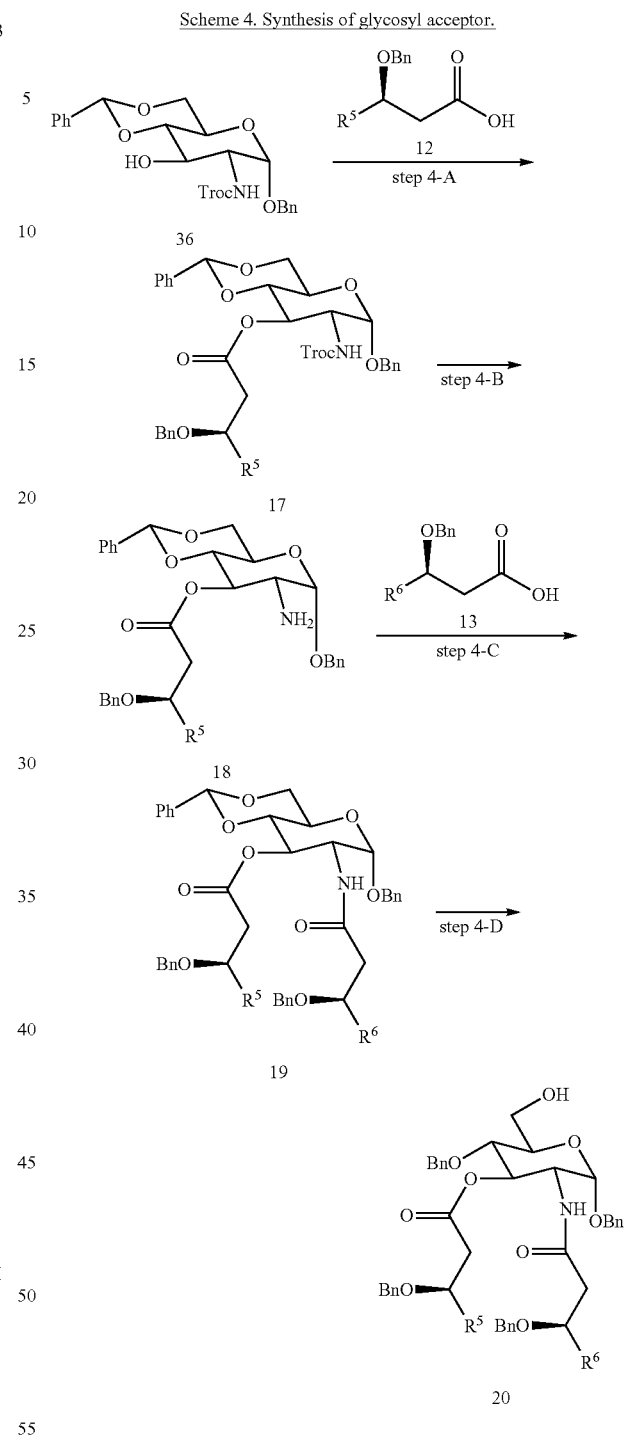

Scheme 3 depicts an exemplary synthesis of glycosyl donor 16. The synthesis of compound 38 is described in the Examples. In step 3-A, compound 38 is esterified with intermediate 8 to form intermediate 14. In step 3-B, intermediate 14 is deprotected to give intermediate 15, which is reacted with trichloroacetonitrile in step 3-C to give trichloroacetimidate 16. One of ordinary skill in the art will appreciate that compound 38 is exemplary, and that other protecting groups may be employed to carry out the synthesis described in Scheme 3 and others.

Scheme 4 depicts an exemplary synthesis of glycosyl acceptor 20. The synthesis of compound 36 is described in the Examples. In step 4-A, compound 36 is esterified with intermediate 12 to form intermediate 17. In step 4-B, intermediate 17 is deprotected to give intermediate 18, which is reacted with intermediate 13 under amide bond forming conditions in step 4-C to given intermediate 19. In step 4-D, the acetal group of intermediate 19 is cleaved to form intermediate 20. One of ordinary skill in the art will appreciate that compound 36 is exemplary, and that other protecting groups may be employed to carry out the synthesis described in Scheme 4 and others.

Scheme 5 depicts an exemplary synthesis of a compound of formula I having a particular stereochemistry, referred to herein as formula I-a. One of ordinary skill in the art will appreciate that the synthetic strategy shown in Schemes 1-5 may be applied to any compound of formula I or II. In step 5-A, intermediates 16 and 20 are reacted under glycosylating conditions to give intermediate 21. In certain embodiments, triflic acid is used to effect the glycosylation. In certain embodiments, trimethylsilyl triflate or boron trifluoride etherate is used in the glycosylation step. In step 5-B, intermediate 21 is deprotected to give intermediate 22, which is reacted with intermediate 9 under amide bond forming conditions in step 5-C to give intermediate 23. In step 5-D, the acetal group of intermediate 23 is cleaved to form intermediate 24. A phosphate group is installed in step 5-E. In some embodiments, a phosphate triester is installed, which is then oxidized to form a protected phosphate group. In some embodiments, a dibenzyl dialkylphosphoramidite reagent is used in the presence of a base such as tetrazole to form a phosphate triester. In some embodiments, a phosphate triester is oxidized using m-CPBA. In some embodiments, a phosphate triester is oxidized using t-BuOOH. In step 5-F, intermediate 24 is globally deprotected to yield a compound of formula I-a. In some embodiments, the global deprotection is effected using hydrogen and palladium on carbon. In some embodiments, global deprotection is effected via transfer hydrogenation.

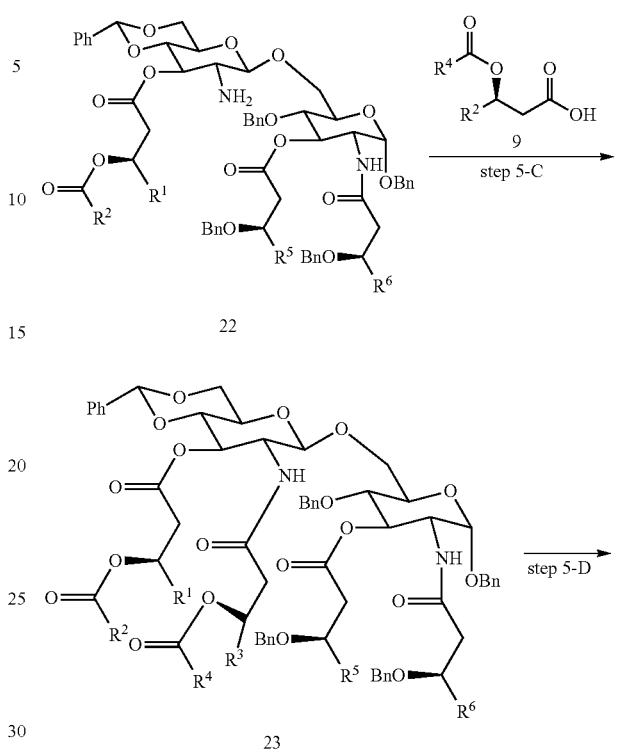

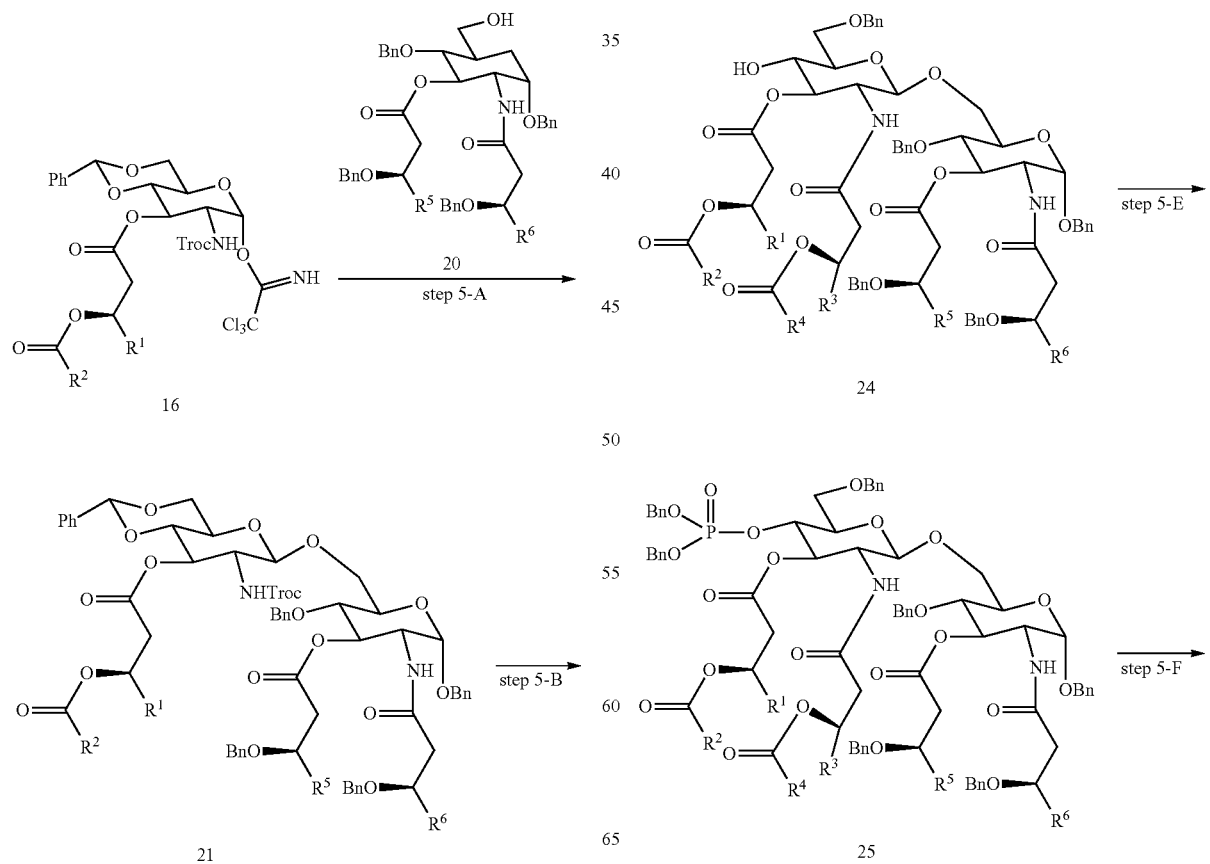

Scheme 5. Synthesis of MPL derivative.

-continued

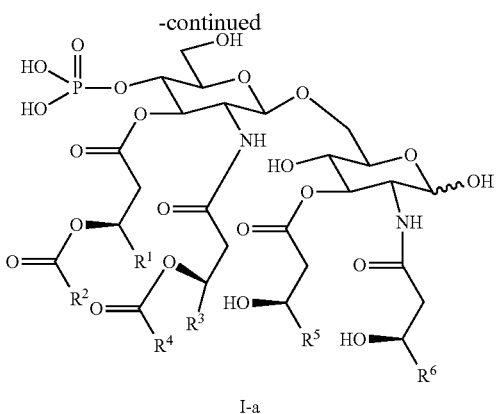

I-a

II. Compositions

In another aspect, the present disclosure provides compositions that include a compound of formula I or II and an antigen. In general it is to be understood that any antigen or antigens may be used in accordance with the present disclosure. Compositions of the present disclosure may also include a vesicle. In certain embodiments, antigen or antigens may be entrapped by vesicles. In general it is also to be understood that in some embodiments, compositions may include amounts of one or more antigens that are not entrapped by vesicles.

Antigens

In some embodiments, compositions in accordance with the present disclosure may include one or more of the antigens currently included in a licensed vaccine. Table 1 is a non-limiting list of suitable licensed vaccines.

TABLE 1

| Vaccine | Disease |
| --- | --- |
| BioThrax ® | Anthrax |
| DTaP (Daptacel ®, Infanrix ®, Tripedia ®) | Diphtheria |
| Td (Decavac ®) | Diphtheria |
| DT, TT | Diphtheria |
| Tdap (Boostrix ®, Adacel ®) | Diphtheria |
| DTaP/IPV/HepB (Pediarix ®) | Diphtheria |
| DTaP/Hib (TriHIBit ®) | Diphtheria |
| Cholera WC/rBS (Dukoral ®) | Enterotoxigenic *Escherichia coli* |
| *Campylobacter*, *Shigella* and ETEC (Activax ®) | Traveler's Diarrhea |
| HepA (Havrix ®, Vaqta ®) | Hepatitis A |
| HepA/HepB (Twinrix ®) | Hepatitis A |
| HepB (Engerix-B ®, Recombivax HB ®) | Hepatitis B |
| HepB/Hib (Comvax) | Hepatitis B |
| DTaP/IPV/HepB (Pediarix), | Hepatitis B |
| HepA/HepB (Twinrix ®) | Hepatitis B |
| Hib (ActHIB ®, HibTITER ®, PedvaxHIB ®) | HIB |
| HepB/Hib (Comvax ®) | HIB |
| DTaP/Hib (TriHIBit ®) | HIB |
| HPV (Gardasil ®) | HPV |
| Influenza (Afluria ®) | Seasonal influenza |
| Influenza (Agriflu ®) | Seasonal influenza |
| Influenza (Begrivac ®) | Seasonal influenza |
| Influenza (Enzira ®) | Seasonal influenza |
| Influenza (Fluad ®) | Seasonal influenza |
| Influenza (Fluarix ®) | Seasonal influenza |
| Influenza (FluLaval ®) | Seasonal influenza |
| Influenza (FluMist ®) | Seasonal influenza |
| Influenza (Fluvax ®) | Seasonal influenza |
| Influenza (FluViral, FluViral S/F ®) | Seasonal influenza |
| Influenza (Fluvirin ®) | Seasonal influenza |
| Influenza (Fluzone ®) | Seasonal influenza |
| Influenza (Grippol ®) | Seasonal influenza |
| Influenza (Inflexal, Inflexal S, | Seasonal influenza |

TABLE 1-continued

| Vaccine | Disease |
| --- | --- |
| Inflexal V ®) | |
| Influenza (Influvac ®) | Seasonal influenza |
| Influenza (Mastaflu ®) | Seasonal influenza |
| Influenza (Mutagrip ®) | Seasonal influenza |
| Influenza (Optaflu ®) | Seasonal influenza |
| Influenza (Vaxigrip ®) | Seasonal influenza |
| H1N1 pandemic influenza (Arepanrix ®) | H1N1 pandemic influenza |
| H1N1 pandemic influenza (Calvapan ®) | H1N1 pandemic influenza |
| H1N1 pandemic influenza (Focetria ®) | H1N1 pandemic influenza |
| H1N1 pandemic influenza (Influenza A (H1N1) 2009 Monovalent Vaccine ®) | H1N1 pandemic influenza |
| H1N1 pandemic influenza (Pandemrix ®) | H1N1 pandemic influenza |
| JE (JE-Vax ®) | Japanese Encephalitis |
| Lyme Disease (LYMErix ®) | Lyme Disease |
| Measles (Attenuvax ®) | Measles |
| Measles (Diplovax HDC 4.0 ®) | Measles |
| Measles (Morbilvax ®) | Measles |
| Measles (Rimevax ®) | Measles |
| Measles and Rubella (M-R Vax, MR-VaxII ®) | Measles and Rubella |
| Measles and Rubella (Moru-Viraten ®) | Measles and Rubella |
| Measles and Mumps (M-M-Rvax ®) | Measles and Mumps |
| MMR (M-M-R II ®) | Measles, Mumps and Rubella |
| MMR (M-M-RvaxPRO ®) | Measles, Mumps and Rubella |
| MMR (Priorix ®) | Measles, Mumps and Rubella |
| MMR (Trimovax ®) | Measles, Mumps and Rubella |
| MMR (Triviraten Berna ®) | Measles, Mumps and Rubella |
| MMRV (ProQuad ®) | Measles, Mumps, Rubella and Varicella |
| Mening. Conjugate (Menactra ®) | Meningococcal |
| Mening. Polysaccharide (Menomune ®) | Meningococcal |
| Mening. Polysaccharide (ACWY Vax ®) | Meningococcal |
| Mening. Polysaccharide (Imovax Meningo A & C ®) | Meningococcal |
| Mening. Polysaccharide (Mencevax ®) | Meningococcal |
| Mening. Polysaccharide (Meningitec ®) | Meningococcal |
| Mening. Polysaccharide (Menjugate ®) | Meningococcal |
| Mening. Polysaccharide (Neisvac-C ®) | Meningococcal |
| Mumps (Mumpsvax ®) | Mumps |
| Mumps and Rubella (Rubilin ®) | Mumps and Rubella |
| MMRV (ProQuad ®) | Mumps |
| DTaP (Daptacel ®, Infanrix ®, Tripedia ®) | Pertussis |
| Tdap (Boostrix ®) | Pertussis |
| DTaP/IPV/HepB (Pediarix ®) | Pertussis |
| DTaP/Hib (TriHIBit ®) | Pertussis |
| Pneumo. Conjugate (Prevnar ®) | Pneumococcal |
| Pneumo. Polysaccharide (Pneumovax 23 ®) | Pneumococcal |
| Pneumo. Conjugate (Pneumovax II ®) | Pneumococcal |
| Pneumo. Polysaccharide (Pnu-Immune 23 ®) | Pneumococcal |
| Polio (Ipol ®) | Polio |
| DTaP/IPV/HepB (Pediarix ®) | Polio |
| Rabies (BioRab ®, Imovax Rabies ®, RabAvert ®) | Rabies |
| Rotavirus (RotaTeq ®) | Rotavirus |
| Rubella (Meruvax II ®) | Rubella |
| Rubella (Ervevax ®) | Rubella |
| Rubella (R-Vac ®) | Rubella |
| *Shigella* Ipa and Polysaccharide (Invaplex ®) | *Shigella* |
| Shingles (Zostavax ®) | Shingles |
| *Vaccinia* (Dryvax ®) | Smallpox and Monkeypox |
| DTaP (Daptacel ®, Infanrix ®, Tripedia ®) | Tetanus |
| Td (Decavac ®) | Tetanus |
| DT, TT | Tetanus |
| Tdap (Boostrix ®) | Tetanus |
| DTaP/IPV/HepB (Pediarix ®) | Tetanus |
| DTaP/Hib (TriHIBit ®) | Tetanus |
| BCG | Tuberculosis |
| Typhoid (Typhim Vi ®) | Typhoid |
| Typhoid oral (Vivotif Berna ®) | Typhoid |
| Varicella (Varivax ®) | Chickenpox (Varicella) |
| MMRV (ProQuad ®) | Chickenpox (Varicella) |
| Yellow Fever (YF-Vax ®) | Yellow Fever |

In the following sections we discuss these and other exemplary antigens that could be used in compositions and methods of the present disclosure.

Hepatitis A

Hepatitis A is a serious liver disease caused by the hepatitis A virus (HAV). The virus is found in the stools of persons with hepatitis A. As shown in Table 1, several inactivated hepatitis A vaccines are currently licensed. For example, Havrix® is manufactured by GlaxoSmithKline Biologicals. U.S. Pat. No. 6,180,110 describes the attenuated HAV strain (HAV 4380) used in Havrix® which was originally derived from the HM175 strain of HAV (U.S. Pat. No. 4,894,228). Havrix® contains a sterile suspension of formalin inactivated HAV. The viral antigen activity is referenced to a standard using an ELISA and expressed in terms of ELISA Units (U). Each 1 ml adult dose of vaccine consists of 1440 U of viral antigen, adsorbed on 0.5 mg of aluminum as aluminum hydroxide (alum). Havrix® (as with all other licensed hepatitis A vaccines) is supplied as a sterile suspension for intramuscular (IM) administration. Although one dose of Havrix® provides at least short-term protection, a second booster dose after six to twelve months is currently recommended to ensure long-term protection.

Another example of an inactivated hepatitis A vaccine, AIMMUGEN® has been licensed and marketed in Japan since 1994 by Kaketsuken. AIMMUGEN® contains a sterile suspension of formaldehyde inactivated HAV. The recommended adult dose is 0.5 μg IM at 0, 1 and 6 months.

As used herein the expression "HAV antigen" or "hepatitis A viral antigen" refers to any antigen capable of stimulating neutralizing antibody to HAV in humans. The HAV antigen may comprise live attenuated virus particles or inactivated virus particles or may be, for example an HAV capsid or HAV viral protein, which may conveniently be obtained by recombinant DNA technology.

In one aspect, the present disclosure provides methods for preparing immunogenic formulations that include an inactivated hepatitis A virus. In general, these methods will involve propagating a hepatitis A virus in a host cell, lyzing the host cell to release the virus, isolating and then inactivating the viral antigen. After removal of the cell culture medium, the cells are lysed to form a suspension. This suspension is purified through ultrafiltration and gel permeation chromatography procedures. The purified lysate is then treated with formalin to ensure viral inactivation (e.g., see Andre et al., *Prog. Med. Virol.* 37:72-95, 1990).

In preparing AIMMUGEN®, hepatitis A virus strain KRM0003 (established from a wild-type HAV, which had been isolated from the feces of a hepatitis A patient) is propagated in GL37 cells (a cell strain established for vaccine production from a parent cell strain of African green monkey kidney). The GL37 cells are inoculated with HAV strain KRM0003 and viral antigen is harvested, extensively purified and inactivated with formaldehyde.

Another example of an inactivated hepatitis A virus that is commercially available but is not a licensed vaccine is hepatitis A antigen (HAV-ag) from Meridian Life Sciences. Like Havrix® the Meridian HAV-ag also derives from hepatitis A virus strain HM175 but it is propagated in FRhK-4 (fetal rhesus kidney) cells. After removal of cell culture medium, the cells are lysed to form a suspension and the suspension is partially purified by gradient centrifugation and inactivated by treatment with formalin.

It will be appreciated that any hepatitis A virus strain may be used, e.g., without limitation any of the following strains which have been described in the art (and other non-human variants):

Human hepatitis A virus Hu/Arizona/HAS-15/1979
Human hepatitis A virus Hu/Australia/HM175/1976
Human hepatitis A virus Hu/China/H2/1982
Human hepatitis A virus Hu/Costa Rica/CR326/1960
Human hepatitis A virus Hu/France/CF-53/1979
Human hepatitis A virus Hu/Georgia/GA76/1976
Human hepatitis A virus Hu/Germany/GBM/1976
Human hepatitis A virus Hu/Japan/HAJ85-1/1985
Human hepatitis A virus Hu/Los Angelos/LA/1975
Human hepatitis A virus Hu/Northern Africa/MBB/1978
Human hepatitis A virus Hu/Norway/NOR-21/1998
Human hepatitis A virus Hu/Sierra Leone/SLF88/1988
Human hepatitis A virus MSM1
Human hepatitis A virus Shanghai/LCDC-1/1984

In addition, while formalin and formaldehyde are commonly used to inactivate licensed hepatitis A vaccines it is to be understood that other techniques could be used, e.g., treatment with chlorine, exposure to high temperatures (the viral antigen is inactivated above 85° C./185° F.), etc.

In certain embodiments it may prove advantageous to add additional steps to the traditional method for preparing an inactivated hepatitis A virus. For example, U.S. Pat. No. 6,991,929 describes including a protease treatment step (e.g., trypsin) after the virus has been propagated. This step was found to improve the removal of host cell material and yield a purer viral preparation.

In one aspect, the present disclosure provides methods for preparing immunogenic formulations that include an attenuated hepatitis A virus. While all currently licensed hepatitis A vaccines include inactivated viral antigens, alternative vaccines which include attenuated viral antigen have also been described in the literature. As is well known in the art, the advantage of an attenuated vaccine lies in the potential for higher immunogenicity which results from its ability to replicate in vivo without causing a full infection.

One method which has been used in the art to prepare attenuated hepatitis A viruses is viral adaptation which involves serially passing a viral strain through multiple cell cultures. Over time the strain mutates and attenuated strains can then be identified. In certain embodiments the virus may be passed through different cell cultures. For example, researchers have generated attenuated hepatitis A viruses by passing strain CR326 sixteen times in human diploid lung (MRCS) cell cultures (see Provost et al., *J. Med. Virol.* 20:165-175, 2005). A slightly more virulent strain was obtained by passing the same strain fifteen times in fetal rhesus monkey kidney (FRhK6) cell cultures plus eight times in MRCS cell cultures. An alternative attenuated hepatitis A vaccine which was prepared in this fashion from the H2 strain has also been described (see European Patent No. 0413637 and Mao et al., *Vaccine* 15:944-947, 1997).

In certain embodiments it may prove advantageous to perform one or more of the cell culture steps at a reduced temperature. For example, European Patent No. 0413637 describes including one or more inoculation steps in which the temperature is reduced (e.g., to 32-34° C. instead of 35-36° C.).

U.S. Pat. No. 6,180,110 describes an attenuated hepatitis A virus (HAV 4380) which grows in MRC-5 cells. The researchers identified mutations in HAV 4380 which appeared to be associated with attenuation by comparing its genome with the genome of a more virulent strain. This allowed them to design mutant HAV strains with optimal characteristics for a candidate attenuated hepatitis A vaccine. It will be appreciated that this approach could be applied to any known attenuated hepatitis A virus and used to genetically engineer variants without the need for viral adaptation.

Hepatitis B

Hepatitis B virus (HBV) causes both acute and chronic infections. The wide clinical spectrum of HBV infection ranges from sub clinical to acute symptomatic hepatitis; from an inactive hepatitis B surface antigen (HBsAg) carrier state to liver cirrhosis and its complications during chronic phase (Fattovich, *J. Hepatol.* 39:s50-58, 2003). HBV is transmitted on parenteral or mucosal exposure to HBsAg positive body fluids generally from HBV infected persons (Hilleman, *Vaccine* 21:4626-4649, 2003).

Currently, there are two commercial vaccines used to prevent HBV infection, both are manufactured using recombinant technology. For example, Engerix-B™ is a noninfectious recombinant DNA hepatitis B vaccine developed by GlaxoSmithKline Biologicals. It contains purified surface antigen of HBV obtained by culturing genetically engineered *Saccharomyces cervisiae* cells, which carry the surface antigen gene of HBV.

As used herein the expression "Hepatitis B surface antigen" or "HBsAg" refers to any HBsAg antigen or fragment thereof displaying the antigenicity of HBV surface antigen in humans.

Engerix-B™ and other licensed hepatitis B vaccines, which are administered parentally, have been successful in inducing a systemic immune response to HBV. However, the antibodies produced as part of the systemic immune response are unable to provide protection at the level of mucosa, which is the major entry site for most infectious agents including HBV. There therefore remains a need in the art for an orally delivered hepatitis B vaccine.

In one aspect, the present disclosure provides methods for preparing immunogenic formulations that include a hepatitis B virus surface antigen or a fragment thereof displaying the antigenicity of HBsAg. All known hepatitis B vaccines include a recombinant HBsAg. It is to be understood that any one of these licensed hepatitis B vaccines may be used as a source of antigen in a method of the present disclosure to produce an immunogenic formulation.

In general, any method may be used to prepare hepatitis B surface antigen. The preparation of HBsAg is well documented (e.g., see Harford et al., *Develop. Biol. Standard* 54: 125, 1983 and Gregg et al., *Biotechnology* 5:479, 1987 among others). In general, recombinant DNA technology methods may be used which involve culturing genetically engineered cells, which carry the surface antigen gene of HBV. The surface antigen expressed is then purified and normally formulated as a suspension of the surface antigen adsorbed on aluminum hydroxide (e.g., see Valenzuela et al., *Proc. Natl. Acad. Sci. USA* 80:1-5, 1983 and McAleer et al., *Nature* 307:178-180, 1984).

Influenza

Influenza is a common infectious disease of the respiratory system associated with the Orthomyxoviridae family of viruses. Influenza A and B are the two types of influenza viruses that cause epidemic human disease. Influenza A viruses are further categorized into subtypes on the basis of two surface antigens: hemagglutinin (HA) and neuraminidase (N). Influenza B viruses are not categorized into subtypes. Vaccination is recognized as the single most effective way of preventing or attenuating influenza for those at high risk of serious illness from influenza infection and related complications. The inoculation of antigen prepared from inactivated influenza virus stimulates the production of specific antibodies. Protection is generally afforded only against those strains of virus from which the vaccine is prepared or closely related strains.

Influenza vaccines, of all kinds, are usually trivalent vaccines. They generally contain antigens derived from two influenza A virus strains and one influenza B strain. The influenza virus strains to be incorporated into influenza vaccines each season are determined by the World Health Organization (WHO) in collaboration with national health authorities and vaccine manufacturers. It will be appreciated that any influenza virus strain may be used in accordance with the present disclosure, and that influenza virus strains will differ from year to year based on WHO recommendations.

Monovalent vaccines, which may be useful for example in a pandemic situation, are also encompassed. A monovalent, pandemic flu vaccine will most likely contain influenza antigen from a single A strain. In some embodiments, influenza antigens are derived from pandemic influenza strains. For example, in some embodiments, influenza antigens are influenza A (H1N1 of swine origin) viral antigens.

Predominantly three types of inactivated vaccines are used worldwide to protect against influenza: whole virus vaccines, split virus vaccines containing external and internal components of the virus, and subunit vaccines composed of just external components of the virus (hemagglutinin and neuraminidase). Without wishing to be limited to any theory, it is thought that the higher purity of subunit vaccines should make them less reactogenic and better tolerated. Conversely whole virus and split virus vaccines are thought to contain more epitopes and so be more immunogenic.

In some embodiments, influenza antigens are based on subunit vaccines. Generally, subunit vaccines contain only those parts of the influenza virus that are needed for effective vaccination (e.g., eliciting a protective immune response). In some embodiments, subunit influenza antigens are prepared from virus particles (e.g., purification of particular components of the virus). In some embodiments, subunit influenza antigens are prepared by recombinant methods (e.g., expression in cell culture). For example, U.S. Pat. No. 5,858,368 describes methods of preparing a recombinant influenza vaccine using recombinant DNA technology. The resulting trivalent influenza vaccine is based on a mixture of recombinant hemagglutinin antigens cloned from influenza viruses having epidemic potential. The recombinant hemagglutinin antigens are full length, uncleaved, glycoproteins produced from baculovirus expression vectors in cultured insect cells and purified under non-denaturing conditions. In some embodiments, subunit influenza antigens are generated by synthetic methods (e.g., peptide synthesis). Subunit vaccines may contain purified surface antigens, hemagglutinin antigens and neuraminidase antigens prepared from selected strains determined by the WHO. Without wishing to be bound by any theories, it is thought that surface antigens, hemagglutinin antigens and neuramidase antigens play a significant role in eliciting production of virus neutralizing antibodies upon vaccination.

In some embodiments, influenza antigens are split virus antigens. Vaccines prepared using split virus antigens typically contain a higher concentration of the most immunogenic portions of the virus (e.g., hemagglutinin and neuramidase), while lowering the concentration of less immunogenic viral proteins as well as non-viral proteins present from eggs (used to produce virus) or extraneous agents (e.g., avian leukosis virus, other microorganisms and cellular debris). Generally, split virus antigens are prepared by a physical process that involves disrupting the virus particle, generally with an organic solvent or a detergent (e.g., Triton X-100), and separating or purifying the viral proteins to varying extents, such as by centrifugation over a sucrose gradient or passage of allantoic fluid over a chromatographic column. In some embodiments, disruption and separation of virus particles is followed by dialysis or ultrafiltration. Split virus antigens usually contain most or all of the virus structural proteins although not necessarily in the same proportions as they occur in the whole virus. Methods of viral splitting as well as suitable splitting agents are known in the art (see for example U.S. Patent Publication No. 20090155309). In some embodiments, final antigen concentration (e.g., of hemagglutinin and/or neuramidase antigens) of split viral antigen is standardized using methods known in the art (e.g., ELISA).

In some embodiments, influenza antigens are whole virus antigens. It is thought that in unprimed individuals, vaccines prepared with whole virus antigens may be more immunogenic and induce higher protective antibody response at a lower antigen dose than other formulations (e.g., subunit or split virus antigens). However, influenza vaccines that include whole virus antigens can produce more side effects than other formulations.

Influenza viral antigens present in immunogenic formulations described herein may be infectious, inactivated or attenuated.

In certain embodiments, an immunogenic formulation may comprise an inactivated viral antigen. It will be appreciated that any method may be used to prepare an inactivated influenza viral antigen. WO 09/029695 describes exemplary methods for producing a whole inactivated virus vaccine. In general, these methods will involve propagating an influenza virus in a host cell, optionally lysing the host cell to release the virus, isolating and then inactivating the viral antigen. Chemical treatment of virus (e.g., formalin, formaldehyde, among others) is commonly used to inactivate virus for vaccine formulation. However, it is to be understood that other techniques could be used, e.g., treatment with chlorine, exposure to high temperatures, etc. In these treatments the outer virion coat is typically left intact while the replicative function is impaired. Non-replicating virus vaccines preferably contain more antigen than live vaccines that are able to replicate in the host.

In certain embodiments, an immunogenic formulation may comprise an attenuated viral antigen. As is well known in the art, one advantage of a vaccine prepared with an attenuated viral antigen lies in the potential for higher immunogenicity which results from its ability to replicate in vivo without causing a full infection. Live virus vaccines that are prepared from attenuated strains preferably lack pathogenicity but are still able to replicate in the host. One method which has been used in the art to prepare attenuated influenza viral antigens is viral adaptation which involves serially passing a viral strain through multiple cell cultures. Over time the strain mutates and attenuated strains can then be identified. In certain embodiments the virus may be passed through different cell cultures. In certain embodiments it may prove advantageous to perform one or more of the cell culture steps at a reduced temperature.

Several influenza vaccines are currently licensed (see Table 1). For example, Fluzone®, which is a split cell inactivated influenza vaccine, is developed and manufactured by Sanofi Pasteur, Inc. and may be used in accordance with the present disclosure. Fluzone® contains a sterile suspension prepared from influenza viruses propagated in embryonated chicken eggs. The virus-containing fluids are harvested and inactivated with formaldehyde. Influenza virus is concentrated and purified in a linear sucrose density gradient solution using a continuous flow centrifuge. The virus is then chemically disrupted using a nonionic surfactant, octoxinol-9, (Triton® X-100) producing a split viral antigen. The split virus is then further purified by chemical means and suspended in sodium phosphate-buffered isotonic sodium chloride solution. Fluzone® vaccine is then standardized according to requirements for the influenza season and is formulated to contain 45 μg hemagglutinin (HA) per 0.5 mL dose, in the recommended ratio of 15 μg HA each, representative of the three prototype strains (e.g., 2007-2008 vaccine prepared with A/Solomon Islands/3/2006 (H1N1), A/Wisconsin/67/2005 (H3N2) and B/Malaysia/2506/2004 strains). Fluzone® vaccine is formulated for intramuscular injection.

Another example of a licensed influenza vaccine that may be used in accordance with the present disclosure is Vaxigrip®, which is a split cell inactivated influenza vaccine also developed and manufactured by Sanofi Pasteur, Inc. Vaxigrip® is prepared in a similar fashion to the process outlined above for Fluzone® and is similarly formulated for intramuscular injection.

Yet another example of a licensed influenza vaccine that may be used in accordance with the present disclosure is Flumist®. Flumist® is a live, attenuated trivalent vaccine for administration by intranasal spray. The influenza virus strains in Flumist® have three genetic mutations that lead to temperature restricted growth and an attenuated phenotype. The cumulative effect of the antigenic properties and the genetically modified influenza viruses is that they are able to replicate in the nasopharynx and induce protective immunity. In order to produce Flumist®, specific pathogen-free (SPF) eggs are inoculated with each of the appropriate viral strains and incubated to allow vaccine virus replication. The allantoic fluid of these eggs is harvested, pooled and then clarified by filtration. The virus is concentrated by ultracentrifugation and diluted with stabilizing buffer to obtain the final sucrose and potassium phosphate concentrations. Viral harvests are then sterile filtered to produce the monovalent bulks. Monovalent bulks from the three strains are subsequently blended and diluted as required to attain the desired potency with stabilizing buffers to produce the trivalent bulk vaccine. The bulk vaccine is then filled directly into individual sprayers for nasal administration. Each pre-filled refrigerated Flumist® sprayer contains a single 0.2 mL dose. Each 0.2 mL dose contains $10^{6.5-7.5}$ FFU of live attenuated influenza virus reassortants of each of the appropriate three viral strains.

As described above, several influenza vaccines are currently licensed. It is to be understood that any one or combination of these licensed influenza vaccines may be combined with a vesicle as described herein to produce an immunogenic formulation. For example, commercial Fluzone® and/or Vaxigrip® may be combined in this manner to produce an active immunogenic formulation. In some embodiments, licensed influenza vaccines are first purified (e.g., to remove alum adjuvant or other reagents in the vaccine). In some embodiments, licensed influenza vaccines are not purified prior to formulation with a vesicle as described herein.

PCT Patent Application No. PCT/US09/47911 describes some other exemplary influenza antigens that could be used in the methods and formulations of the present disclosure. Exemplary influenza antigens have also been described in U.S. Pat. Nos. 7,527,800; 7,537,768; 7,514,086; 7,510,719; 7,494,659; 7,468,259; 7,399,840; 7,361,352; 7,316,813; 7,262,045; 7,244,435; 7,192,595; 7,052,701; 6,861,244; 6,743,900; 6,740,325; 6,635,246; 6,605,457; 6,534,065; 6,372,223; 6,344,354; 6,287,570; 6,136,606; 5,962,298; 5,948,410; and 5,919,480.

Other Antigens

Although embodiments of the present disclosure may be used with any particular antigen, non-limiting examples of other antigens that may be used with particular embodiments include the following.

Whole killed or inactivated antigens such as those utilized against polio, rabies and other diseases may be included in compositions of the present disclosure. These antigens may be present in vaccines such as Ipol®, DTaP/IPV/HepB (Pediarix®), BioRab®, Imovax Rabies®, RabAvert®, and Havrix®. Other exemplary whole killed or inactivated antigens for use in embodiments of the invention may be derived from *Bordetella pertussis, Vibrio cholerae* and *Salmonella typhi*, and inactivated virus particles.

Additional antigens for use in embodiments of the present disclosure include virus-like particle ("VLP") or synthetic (retroviral) antigens. Virus-like particles imitate natural viruses, typically either through similarities in size and shape or a repetitive pattern of antigenic epitopes. Exemplary VLP vaccines include VLPs of HBV (e.g., Recombivax®, Engerix-B®) and HPV (e.g., Gardasil®). Synthetic retroviral antigens for use in certain embodiments may be based on core protein particles from retroviruses (e.g., MLV) capable of incorporating glycoproteins from different viruses in a phospholipid envelope. The surface proteins are naturally embedded in a phospholipid layer, and therefore provide virus-like size and shape with ordered antigen display. The surface proteins may be customized to provide a natural display of a wide variety of different epitopes. Synthetic antigens can be produced in host by means of expression from DNA vectors or from viral vectors (e.g., Measles virus, Adenovirus, AAV). Synthetic antigens for use in embodiments of the present disclosure may be derived from, for example, HCV, Dengue virus, West Nile virus, Yellow Fever virus, Tickborne Encephalitis virus, HIV, Influenza, Chikungunya, Sindbis, Simliki Forest virus, Measles, Ross River virus, Respiratory syncytial virus, and Parainfluenza viruses, Equine Encephalitis virus, SARS, Ebola virus, Marburg virus and Lassa virus, among others. Synthetic viral compositions and uses of the same to modify or regulate immune response are disclosed in U.S. Patent Publication No. 2004/0071661. Typical examples of such viral antigens include gp 120, gp 160, gag epitopes, V3-loop peptide, etc., derived from HIV; pp65, IEI, gB, pp150, PP28, etc. from cytomegalovirus; gp85, gp340, gp350, p-2B, etc. from EBV.

The present disclosure also encompasses the use of peptide antigens. Peptide antigens are relatively short polypeptide fragments comprising 3 or more amino acids. In certain embodiments the peptide antigens include fewer than 25 amino acids, e.g., fewer than 20, 19, 18, 17, 16, 15, or 10 amino acids. They are frequently derived from epitopes of known antigens or whole cell killed or inactivated antigens, in which case they function essentially as surrogates of their parent antigens. Alternatively or in addition, peptide antigens can elicit novel immune responses via de novo immunogenic potential. Peptide antigens may comprise a pool of different sequences (e.g., in approximately equimolar quantities) that are derived from a common epitope or may consist of a plurality of a single sequence. The peptides do not need to be modified, although in certain embodiments it may be advantageous to modify the peptides by, for example, lipidation. Processes for preparing immunogenic peptides are described in WO/2006/092046 for HIV, and WO/2006/092046 and WO/2008/064488 and WO/2009/155489 for influenza, which are hereby incorporated by reference in their entirety. U.S. Pat. Nos. 6,592,871, 5,939,074, 5,824,506, 7,202,034 disclose exemplary peptide antigens derived from, for example, HCV, HIV, Dengue virus, and HPV that could be used in certain embodiments. Additional antigenic peptides that are encompassed stimulate a T cell-mediated immune response (e.g., a cytotoxic T cell response) by presentation to T cells on MHC molecules. Useful antigenic peptides include those derived from cancer stem cells or other cancerous cells, including those described in U.S. Pat. No. 7,928,190.

Hepatitis C virus (HCV) is now recognized as being the primary cause of transfusion-associated non-A, non-B (NANB) hepatitis. HCV is a single stranded, positive sense RNA virus with similarities to flaviviruses and pestiviruses (Miller et al., *Proc. Natl. Acad. Sci.* 87: 2057, 1991 and Weiner et al., *Virology* 180: 842, 1990). U.S. Pat. Nos. 7,348,011; 6,831,169; 6,538,123 and 6,235,888 all describe exemplary HCV antigens that could be used.

The human immunodeficiency retrovirus (HIV) is responsible for AIDS (acquired immunodeficiency syndrome), a disease in which the body's immune system breaks down leaving it vulnerable to opportunistic infections. U.S. Pat. Nos. 7,067,134; 7,063,849; 6,787,351; 6,706,859; 6,692,955; 6,653,130; 6,649,410; 6,541,003; 6,503,753; 6,500,623; 6,383,806; 6,090,392; 5,861,243; 5,817,318; and 4,983,387 all describe exemplary HIV antigens that could be used. Various HIV antigens are also disclosed in U.S. Patent Application Publication Nos. 2009/0117141 and 2009/0081254.

Vesicles

As mentioned above, compositions of the present disclosure may include a vesicle. As is well known in the art, vesicles generally have an aqueous compartment enclosed by one or more bilayers which include amphipathic molecules (e.g., lipids, steroids, etc.). In certain embodiments, vesicles of the present disclosure comprise a non-ionic surfactant to form a non-ionic surfactant vesicle (NISV).

Non-Ionic Surfactant

Any non-ionic surfactant with appropriate amphipathic properties may be used to form a vesicle. Without limitation, examples of suitable surfactants include ester-linked surfactants based on glycerol. Such glycerol esters may comprise one of two higher aliphatic acyl groups, e.g., containing at least ten carbon atoms in each acyl moiety. Surfactants based on such glycerol esters may comprise more than one glycerol unit, e.g., up to 5 glycerol units. Glycerol monoesters may be used, e.g., those containing a $C_{12}$-$C_{20}$ alkanoyl or alkenoyl moiety, for example caproyl, lauroyl, myristoyl, palmitoyl, oleyl or stearoyl. An exemplary surfactant is 1-monopalmitoyl glycerol.

Ether-linked surfactants may also be used as the non-ionic surfactant. For example, ether-linked surfactants based on glycerol or a glycol having a lower aliphatic glycol of up to 4 carbon atoms, such as ethylene glycol, are suitable. Surfactants based on such glycols may comprise more than one glycol unit, e.g., up to 5 glycol units (e.g., diglycolcetyl ether and/or polyoxyethylene-3-lauryl ether). Glycol or glycerol monoethers may be used, including those containing a $C_{12}$-$C_{20}$ alkanyl or alkenyl moiety, for example capryl, lauryl, myristyl, cetyl, oleyl or stearyl. Ethylene oxide condensation products that can be used include those disclosed in PCT Publication No. WO88/06882 (e.g., polyoxyethylene higher aliphatic ether and amine surfactants). Exemplary ether-linked surfactants include 1-monocetyl glycerol ether and diglycolcetyl ether.

Other Vesicle Components

In some embodiments, vesicles may include an ionic surfactant, e.g., to cause the vesicles to take on a negative charge. For example, this may help to stabilize the vesicles and provide effective dispersion. Without limitation, acidic materials such as higher alkanoic and alkenoic acids (e.g., palmitic acid, oleic acid) or other compounds containing acidic groups including phosphates such as dialkyl phosphates (e.g., dicetylphospate, or phosphatidic acid or phosphatidyl serine) and sulphate monoesters such as higher alkyl sulphates (e.g., cetylsulphate), may all be used for this purpose. The ionic surfactant(s), if present, will typically comprise, between 1 and 50% by weight of the non-ionic surfactant (e.g., between 1 and 35% by weight, between 5 and 40% by weight, between 10 and 40% by weight, between 15 and 40% by weight, between 20 and 40% by weight, or between 20 and 35% by weight).

In some embodiments, the vesicles may include an appropriate hydrophobic material of higher molecular mass that facilitates the formation of bilayers (such as a steroid, e.g., a sterol such as cholesterol). In some embodiments, the presence of the steroid may assist in forming the bilayer on which the physical properties of the vesicle depend. The steroid, if present, will typically comprise between 20 and 120% by weight of the non-ionic surfactant. For example, between 25 and 90% by weight or between 35 and 75% by weight. In some embodiments, the steroid, if present, will comprise between 25 and 95% by weight, between 25 and 105% by weight, between 35 and 95% by weight, or between 35 and 105% by weight of the non-ionic surfactant.

In some embodiments, a lyoprotectant may be included in the composition. Exemplary lyoprotectants include sucrose, trehalose, polyethylene glycol (PEG), dimethyl-succinate buffer (DMS), bovine serum albumin (BSA), mannitol and dextran.

In some embodiments, the vesicles may include a non-ionic surfactant, an ionic surfactant and an appropriate hydrophobic material of higher molecular mass that facilitates the formation of bilayers (such as a steroid, e.g., a sterol such as cholesterol).

Inverted Melt Method for Making Vesicles

In certain embodiments, vesicles may be made by a method which includes steps of providing a molten mixture that includes the non-ionic surfactant and then adding the molten mixture to an aqueous solution comprising an antigen such that vesicles are formed. In some embodiments, the aqueous solution comprising the antigen is temperature controlled. In some embodiments, the aqueous solution comprising the antigen is kept at a temperature of less than about 50° C. during the step of adding (e.g., less than about 40° C., less than about 30° C., etc.). In some embodiments, the aqueous solution comprising an antigen is kept at a temperature range between about 25° C. and about 50° C. In some embodiments, the aqueous solution comprising an antigen is kept at room temperature. The compound of formula I or II may be included in the molten mixture and/or in the aqueous solution comprising the antigen.

Rehydration Method for Making Vesicles

In certain embodiments, vesicles may be made by a method which includes steps of providing a lyophilized non-ionic surfactant product and rehydrating the lyophilized product with an aqueous solution comprising an antigen such that vesicles are formed. Without wishing to be bound to any theory, it is thought that by adding an aqueous solution of the antigen to the lyophilized product, vesicles are formed in the presence of the antigen. This avoids exposing the antigen to organic solvents and high temperatures. A compound of formula I or II may be included in the lyophilized non-ionic surfactant product and/or in the aqueous solution comprising the antigen. In some embodiments, the lyophilized product is prepared by melting the non-ionic surfactant to produce a molten mixture and then lyophilizing the molten mixture. In some embodiments, the lyophilized product is prepared by dissolving the non-ionic surfactant in a polar-protic water-miscible organic solvent to produce a solution and then lyophilizing the solution.

Protic solvents are solvents that contain dissociable protons (e.g., a hydrogen atom bound to an oxygen as in a hydroxyl group or a nitrogen as in an amine group). In some embodiments, the polar-protic water-miscible organic solvent is an aliphatic alcohol having 3-5 carbon atoms (e.g., 4 carbon atoms). In some embodiments, the solvent is tert-butanol.

In some embodiments, the non-ionic surfactant is dissolved in a polar-protic water-miscible organic solvent without any co-solvents present. In some embodiments, the non-ionic surfactant is dissolved in a polar-protic water-miscible organic solvent with one or more co-solvents present. In some embodiments one or more of the co-solvents are also polar-protic water-miscible organic solvents. In some embodiments, the polar-protic water-miscible organic solvent makes up at least 70% v/v of the solvent system, e.g., at least 75%, 80%, 90%, 95% or 99%. In some embodiments, the non-ionic surfactant is dissolved in a water-free solvent system. In some embodiments, the non-ionic surfactant is dissolved in a solvent system that includes an amount of water such that vesicles do not form. In some embodiments, the non-ionic surfactant is dissolved in a solvent system that includes less than 5% v/v water, e.g., less than 4%, 3%, 2%, 1%, 0.5%, or 0.1%.

As discussed above, the method includes a step of lyophilizing a solution that includes a non-ionic surfactant. Lyophilization is an established method used to enhance the long-term stability of products. Enhancement of physical and chemical stability is thought to be accomplished by preventing degradation and hydrolysis. Lyophilization involves freezing the preparation in question and then reducing the surrounding pressure (and optionally heating the preparation) to allow the frozen solvent(s) to sublime directly from the solid phase to gas (i.e., drying phase). In certain embodiments, the drying phase is divided into primary and secondary drying phases.

The freezing phase can be done by placing the preparation in a container (e.g., a flask, eppendorf tube, etc.) and optionally rotating the container in a bath which is cooled by mechanical refrigeration (e.g., using dry ice and methanol, liquid nitrogen, etc.). In some embodiments, the freezing step involves cooling the preparation to a temperature that is below the eutectic point of the preparation. Since the eutectic point occurs at the lowest temperature where the solid and liquid phase of the preparation can coexist, maintaining the material at a temperature below this point ensures that sublimation rather than evaporation will occur in subsequent steps.

The drying phase (or the primary drying phase when two drying phases are used) involves reducing the pressure and optionally heating the preparation to a point where the solvent(s) can sublimate. This drying phase typically removes the majority of the solvent(s) from the preparation. It will be appreciated that the freezing and drying phases are not necessarily distinct phases but can be combined in any manner. For example, in certain embodiments, the freezing and drying phases may overlap.

A secondary drying phase can optionally be used to remove residual solvent(s) that was adsorbed during the freezing phase. Without wishing to be bound to any theory, this phase involves raising the temperature to break any physico-chemical interactions that have formed between the solvent molecules and the frozen preparation. Once the drying phase is complete, the vacuum can be broken with an inert gas (e.g., nitrogen or helium) before the lyophilized lipid product is optionally sealed.

In some embodiments, the lyophilized product is substantially free of organic solvent(s).

Once the solution has been lyophilized the method includes a step of rehydrating the lyophilized product to form vesicles. This is achieved by mixing the lyophilized product with an aqueous solution comprising the antigen. In some embodiments, this involves adding the aqueous solution to the lyophilized product.

In some embodiments, the aqueous solution includes a buffer. The buffer used will typically depend on the nature of the antigen or antigens in the aqueous solution. For example, without limitation, a PCB buffer, an $Na_2HPO_4/NaH_2PO_4$ buffer, a PBS buffer, a bicine buffer, a Tris buffer, a HEPES buffer, a MOPS buffer, etc. may be used. PCB buffer is produced by mixing sodium propionate, sodium cacodylate, and bis-Tris propane in the molar ratios 2:1:2. Varying the amount of HCl added enables buffering over a pH range from 4-9. In some embodiments, a carbonate buffer may be used.

Other Methods for Making Vesicles

It will be appreciated that there are other known techniques for preparing vesicles comprising non-ionic surfactants, such as those referred to in PCT Publication No. WO93/19781. An exemplary technique is the rotary film evaporation method, in which a film of non-ionic surfactant is prepared by rotary evaporation from an organic solvent, e.g., a hydrocarbon or chlorinated hydrocarbon solvent such as chloroform, e.g., see Russell and Alexander, *J. Immunol.* 140:1274, 1988. The resulting thin film is then rehydrated in bicarbonate buffer in the presence of an antigen. A compound of formula I or II may be included in the original film and/or in the aqueous solution comprising the antigen.

Another method for the production of vesicles is that disclosed by Collins et al., J. Pharm. Pharmacol. 42:53, 1990. This method involves melting the non-ionic surfactant and hydrating with vigorous mixing in the presence of aqueous buffer containing the antigen. The compound of formula I may be included in the original melt and/or in the aqueous solution comprising the antigen.

Another method involves hydration in the presence of shearing forces. An apparatus that can be used to apply such shearing forces is a well known, suitable equipment (see, e.g., PCT Publication No. WO88/06882). Sonication and ultra-sonication are also effective means to form the vesicles or to alter their particle size.

In some embodiments, a composition of the present disclosure may be lyophilized for future use and subsequently hydrated (e.g., with sterile water or an aqueous buffer) prior to use.

Vesicle Size and Processing

It will be appreciated that a composition comprising vesicles will typically include a mixture of vesicles with a range of sizes. It is to be understood that the diameter values listed below correspond to the most frequent diameter within the mixture. In some embodiments >90% of the vesicles in a composition will have a diameter which lies within 50% of the most frequent value (e.g., 1000±500 nm). In some embodiments the distribution may be narrower, e.g., >90% of the vesicles in a composition may have a diameter which lies within 40, 30, 20, 10 or 5% of the most frequent value. In some embodiments, sonication or ultra-sonication may be used to facilitate vesicle formation and/or to alter vesicle size. In some embodiments, filtration, dialysis and/or centrifugation may be used to adjust the vesicle size distribution.

In general, vesicles produced in accordance with the methods of the present disclosure may be of any size. In some embodiments, the compositions may include vesicles with a diameter in the range of about 150 nm to about 15 µm, e.g., about 800 nm to about 1.5 µm. In certain embodiments, the vesicles may have a diameter which is greater than 10 µm, e.g., about 15 µm to about 25 µm. In certain embodiments, the vesicles may have a diameter in the range of about 2 µm to about 10 µm, e.g., about 1 µm to about 4 µm. In certain embodiments, the vesicles may have a diameter which is less than 150 nm, e.g., about 50 nm to about 100 nm.

III. Methods of Use

Immunogenic compositions of the present disclosure are useful for treating many diseases in humans including adults and children. In general however they may be used with any animal. In certain embodiments, the compositions and methods herein may be used for veterinary applications, e.g., canine and feline applications. If desired, the compositions and methods herein may also be used with farm animals, such as ovine, avian, bovine, porcine and equine breeds Immunogenic compositions described herein will generally be administered in such amounts and for such a time as is necessary or sufficient to induce an immune response. Dosing regimens may consist of a single dose or a plurality of doses over a period of time. The exact amount of antigen and/or compound of formula I or II to be administered will vary depending on the nature of the antigen and may vary from patient to patient. Thus, it will be appreciated that, in general, the precise dose used will be as determined by the prescribing physician and will depend not only on the nature of the antigen, the weight of the patient and the route of administration, but also on the frequency of dosing, the age of the patient and the severity of the symptoms and/or the risk of infection.

In general the appropriate dose of antigen in an immunogenic composition will vary depending on the nature of the antigen and the patient being treated; however, in certain embodiments it may range from about 5 µg to about 5 mg, e.g., from about 20 µg to about 2 mg, from about 50 µg to about 1 mg, or from about 100 µg to about 750 µg. Lower doses of antigen may be sufficient when using sublingual or buccal administration, or depending on the presence of and/or amount of compound of formula I or II. Higher doses of antigen may be more useful when given orally, especially with low amounts of a compound of formula I or II. In some embodiments, the orally administered dose of antigen is from about 4 to 10 times higher than the intramuscular administered dose of antigen, e.g., from about 5 to 7 times higher.

In certain embodiments, the dose of a compound of formula I or II in an immunogenic composition may range from about 1-100 µg (e.g., about 1-50 µg, about 1.5-50 µg, about 2.5-50 µg, about 2.5-50 µg, about 2.5-40 µg, about 2.5-30 µg, about 2.5-20 µg, or about 2.5-10 µg).

In certain embodiments, the compositions may be formulated for delivery parenterally, e.g., by injection. In such embodiments, administration may be, for example, intravenous, intramuscular, intradermal, or subcutaneous, or via by infusion or needleless injection techniques. In certain embodiments, the compositions may be formulated for intramuscular delivery. For such parenteral administration, the immunogenic compositions may be prepared and maintained in conventional lyophilized compositions and reconstituted prior to administration with a pharmaceutically acceptable saline solution, such as a 0.9% saline solution. The pH of the injectable composition can be adjusted, as is known in the art, with a pharmaceutically acceptable acid, such as methanesulfonic acid. Other acceptable vehicles and solvents that may be employed include Ringer's solution and U.S.P. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable compositions can be sterilized, for example, by filtration through a bacterial-retaining filter, or by incorporating sterilizing agents in the form of sterile solid compositions which can be dissolved or dispersed in sterile water or other sterile injectable medium prior to use.

The immunogenic compositions may also be administered orally (including buccally, sublingually and by gastric lavage or other artificial feeding means). Such oral delivery may be accomplished using solid or liquid compositions, for example in the form of tablets, capsules, multi-particulates, gels, films, ovules, elixirs, solutions, suspensions, etc. In certain embodiments, when using a liquid composition, the composition may be administered in conjunction with a basic composition (e.g., a bicarbonate solution) in order to neutralize the stomach pH. In certain embodiments, the basic composition may be administered before and/or after the immunogenic composition. In certain embodiments, the basic composition may be combined with the immunogenic composition prior to administration or taken at the same time as the immunogenic composition.

The immunogenic compositions can also be administered intranasally or by inhalation and are conveniently delivered in the form of a dry powder inhaler or an aerosol spray presentation from a pressurized container, pump, spray, atomiser or nebuliser, with or without the use of a suitable propellant, e.g., dichlorodifluoromethane, trichlorofluoromethane, dichlorotetrafluoroethane, a hydrofluoroalkane, carbon dioxide or other suitable gas. In the case of a pressurized aerosol, the dosage unit may be determined by providing a valve to deliver a metered amount. The pressurized container, pump, spray, atomiser or nebuliser may contain a solution or suspension of the antibody, e.g., using a mixture of ethanol and the propellant as the solvent, which may additionally contain a lubricant, e.g., sorbitantrioleate. Capsules and cartridges (made, for example, from gelatin) for use in an inhaler or insufflator may be formulated to contain a powder mix of the immunogenic composition and a suitable powder base such as lactose or starch.

Compositions for rectal administration are preferably suppositories which can be prepared by mixing the immunogenic composition with suitable non-irritating excipients or carriers such as cocoa butter, polyethylene glycol or a suppository wax which are solid at ambient temperature but liquid at body temperature and therefore melt in the rectal vault and release the antibodies. Retention enemas and rectal catheters can also be used as is known in the art. Viscosity-enhancing carriers such as hydroxypropyl cellulose are also certain carriers of the disclosure for rectal administration since they facilitate retention of the composition within the rectum. Generally, the volume of carrier that is added to the composition is selected in order to maximize retention of the composition. In particular, the volume should not be so large as to jeopardize retention of the administered composition in the rectal vault.

EXAMPLES

The following examples describe some exemplary modes of making and practicing certain compositions that are described herein. It should be understood that these examples are for illustrative purposes only and are not meant to limit the scope of the compositions and methods described herein.

Example 1: Synthesis of MPL Derivative

Figure 2:
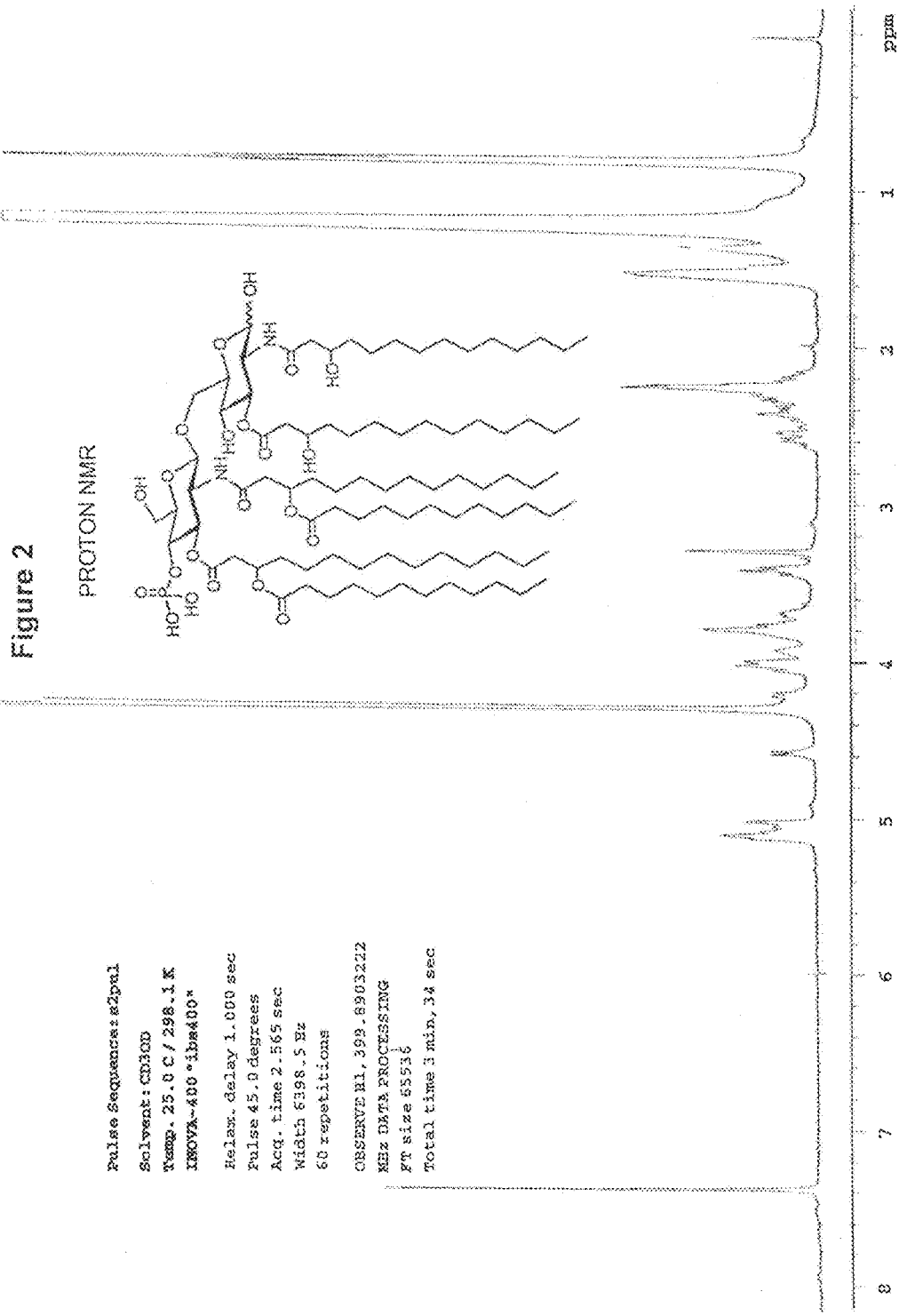
FIG. 2 is an $^1$H NMR spectrum of MAV4.

Schemes 6-11 describe a synthesis that was performed to give an MPL derivative 49 (i.e., MAV4). MALDI-MS of 49 gives an m/z of 1713.1 [M+Na] as shown in FIG. 1. $^1$H NMR spectrum of 49 (400 MHz, CD$_3$OD) is shown in FIG. 2.

Scheme 6. Synthesis of (R)-3-hydroxytetradecanoic acid

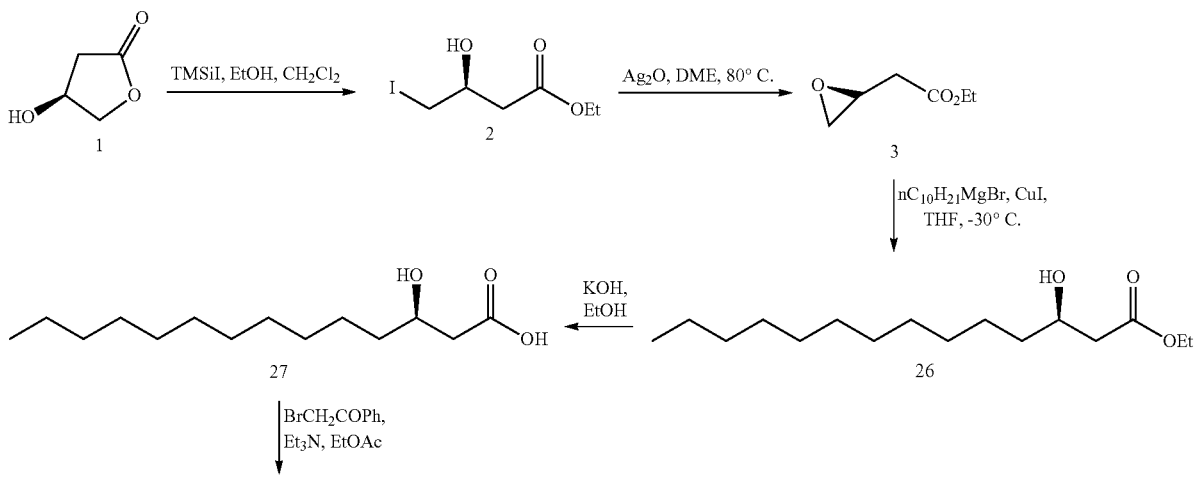

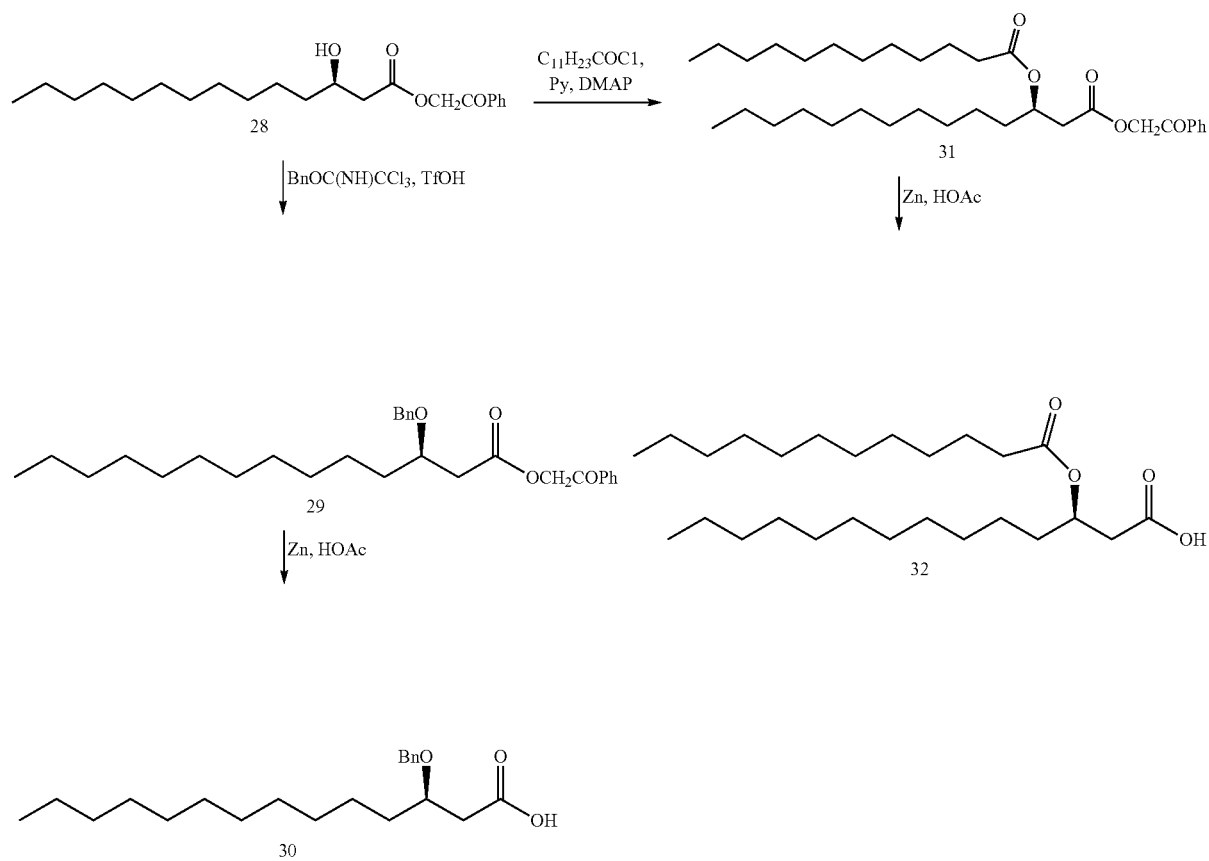
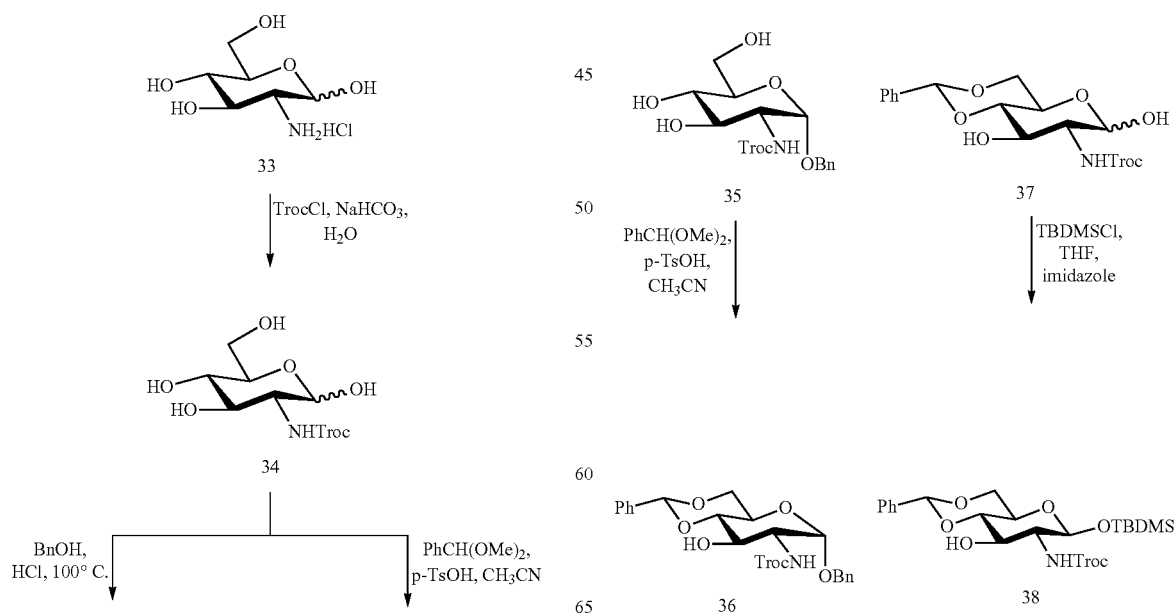
Scheme 7. Synthesis of glucosamine derivatives.

Scheme 8. Synthesis of glycosyl donor.
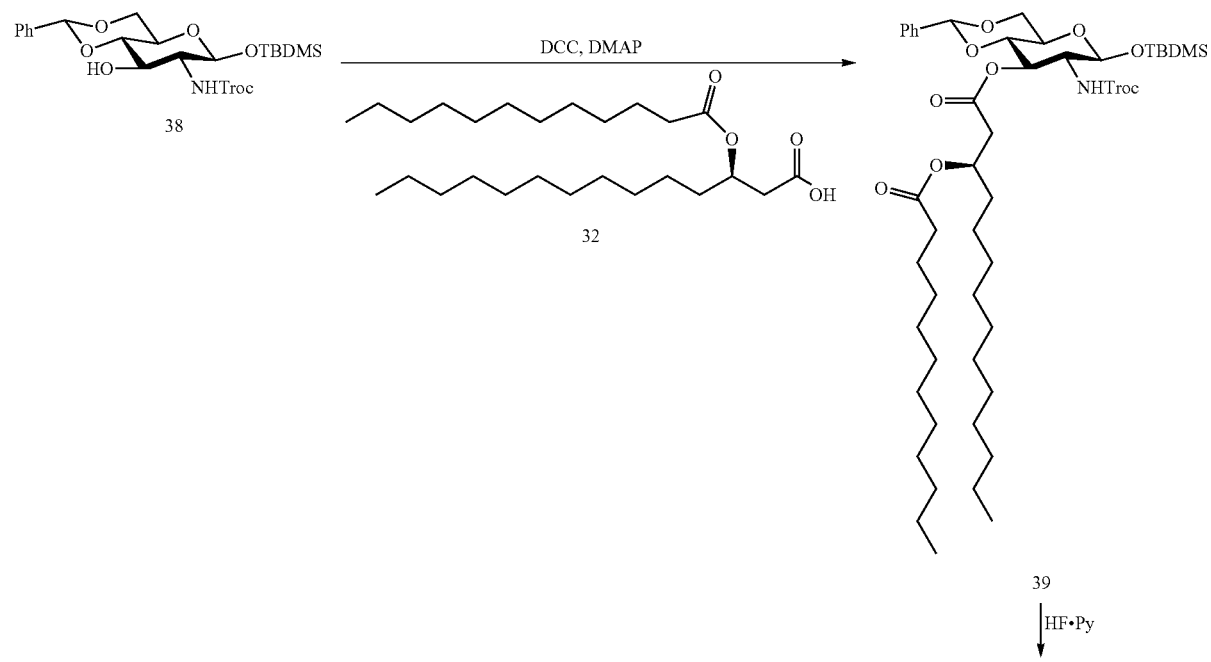
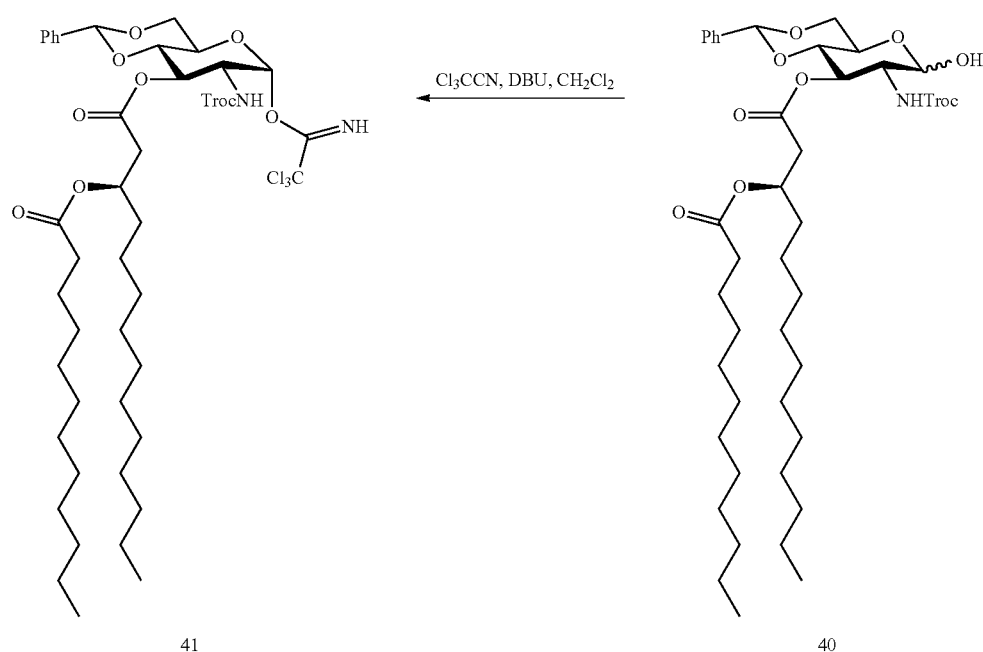

Scheme 9. Synthesis of glycosyl acceptor.
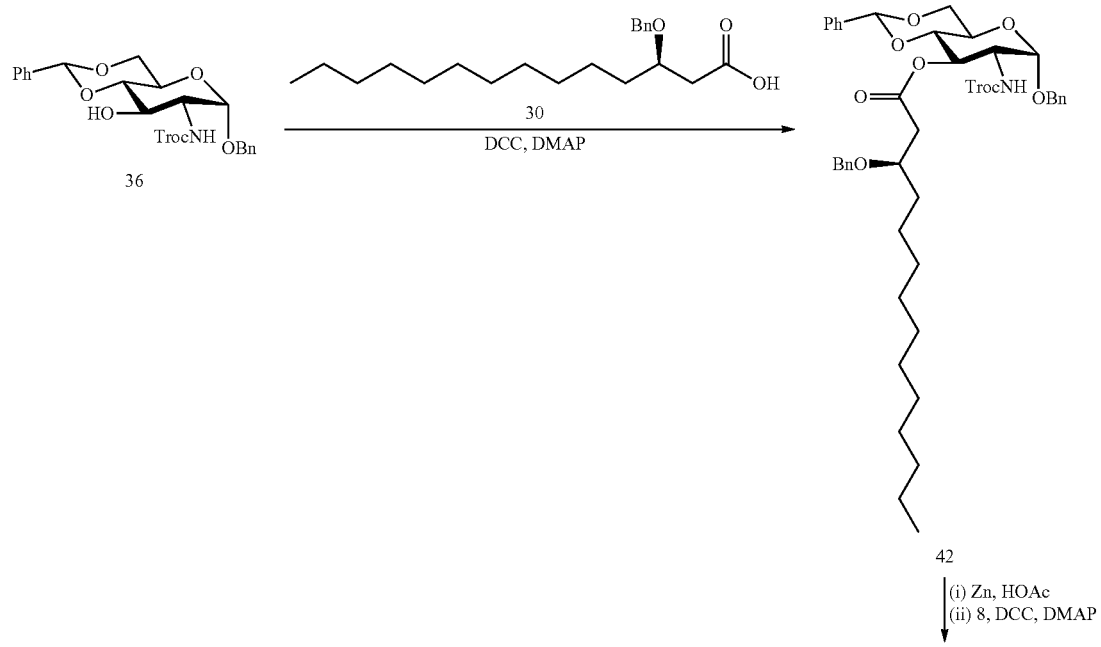
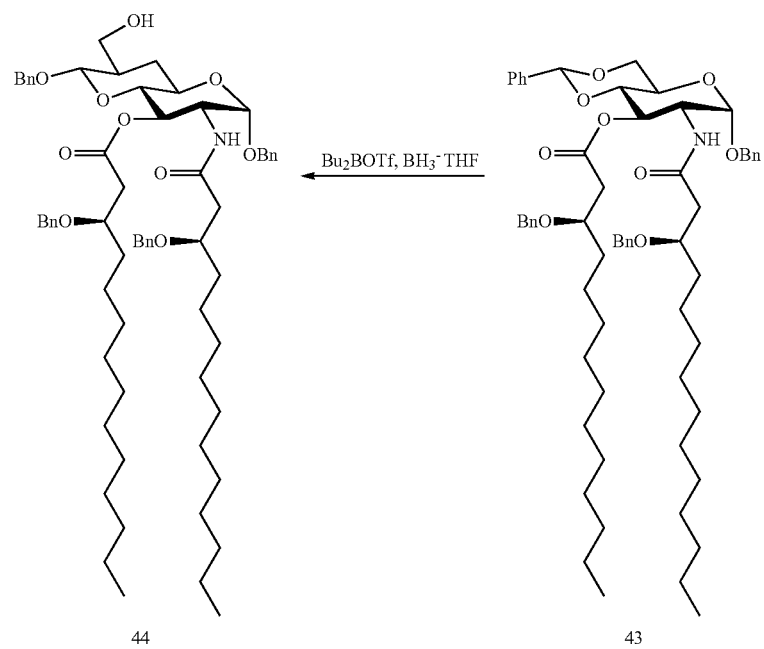

Scheme 10. Synthesis of disaccharide 46.
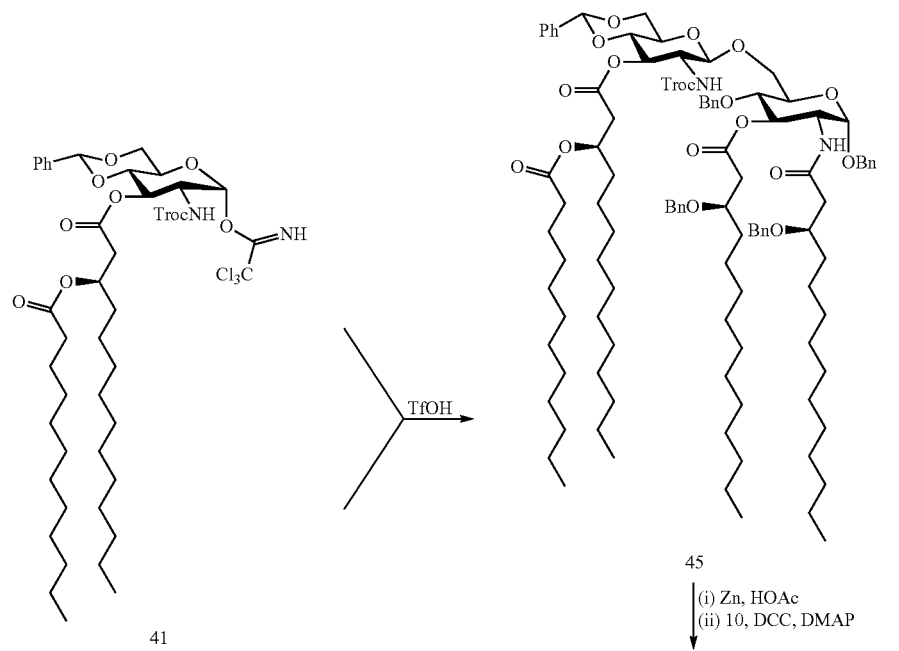
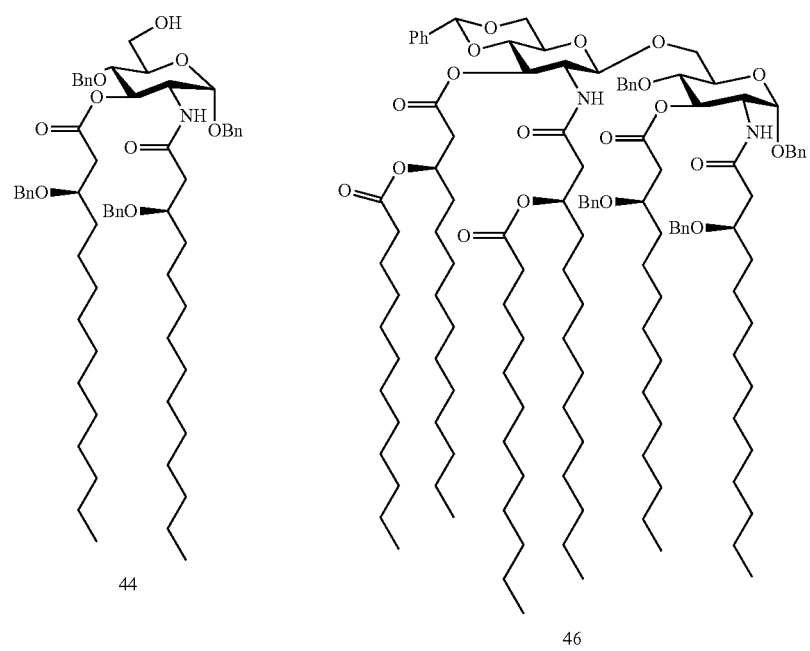

Scheme 11. Synthesis of MPL derivative 49.

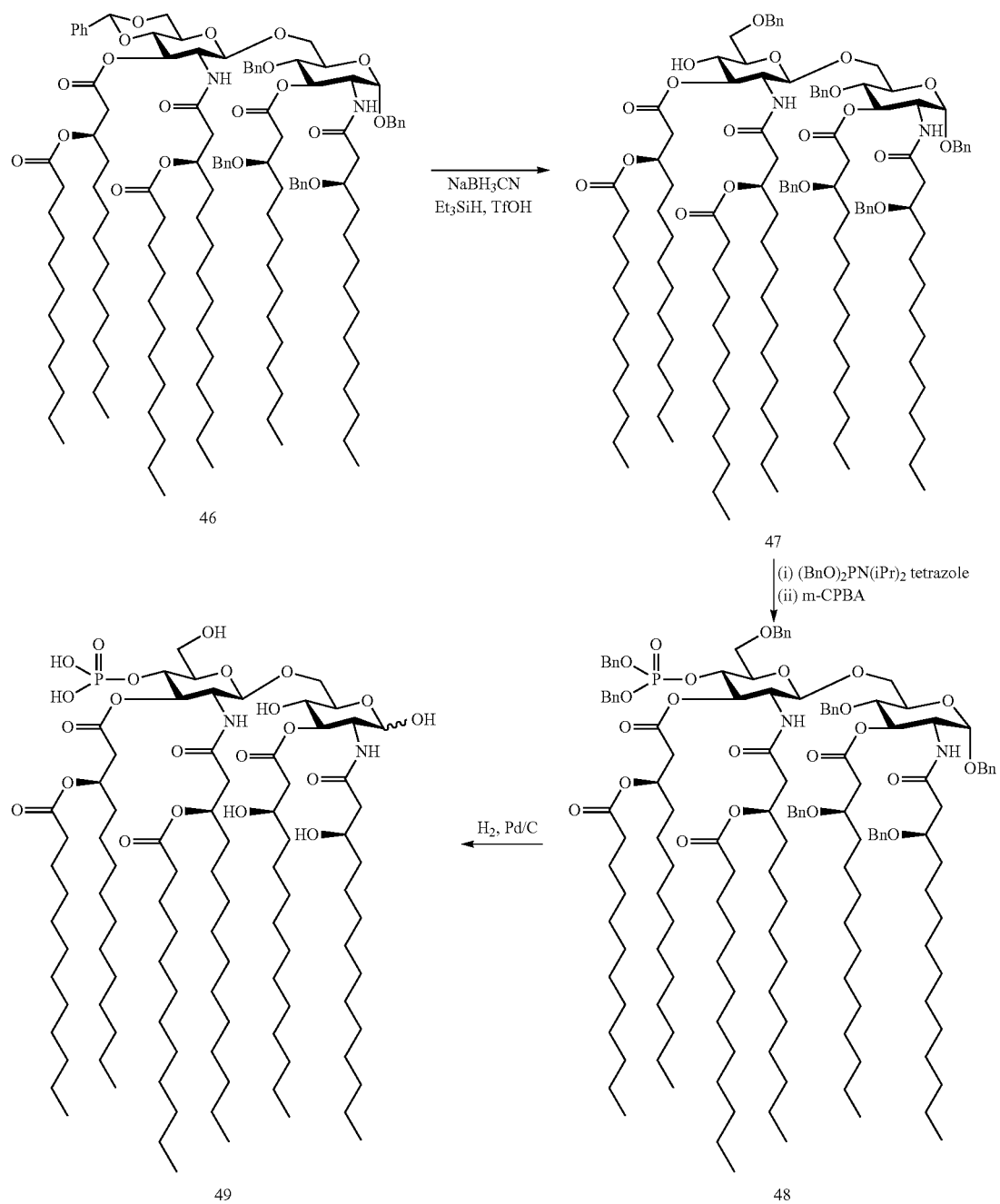

Example 2: Cytokine Induction Assay of MPL Derivative

The BD™ Cytometric Bead Array (CBA) Human inflammatory Cytokines Kit was used to quantitatively measure Tumor Necrosis Factor (TNF a), Interleukin-6 (IL-6) and Interleukin-1β (IL-1β) protein levels in single samples of Human Peripheral Blood Mononuclear Cell (hPBMC) culture supernatants pretreated with either the adjuvant PHAD or MAV4. The detection reagent provided in the kit was a mixture of phycoerythrin (PE)-conjugated antibodies, which provides a fluorescent signal in proportion to the amount of bound cytokine.

When the capture beads and detector reagent are incubated with an unknown sample containing recognized cytokines, sandwich complexes (capture bead+cytokine+detection reagent) are formed. These complexes are measured using flow cytometry. The intensity of PE fluorescence of each sandwich complex reveals the concentration of that cytokine.

To perform the assay lyophilized human inflammatory cytokine standards were reconstituted with assay diluent and serially diluted (standard curve for each protein covers a defined set of concentrations from 20 to 5,000 μg/ml) and test samples were diluted to the desired dilution factor using the assay diluent before mixing all assay tubes with capture beads (50 µl) and PE detection reagent (50 µl). Assay tubes (standards and samples mixed with capture beads and PE detection reagent) were incubated for 3.0 hours at room temperature protected from light. 1 ml of wash buffer was added to each assay tube and the tubes were then centrifuged at 200 g for 5 minutes; supernatant was carefully aspirated leaving approximately 100 µl of liquid in each assay tube. 300 µl of wash buffer was added to each assay tube to resuspend the bead pellet. Samples were then analyzed by flow cytometry and data was analyzed using FCAP Array Software.

Figure 3:
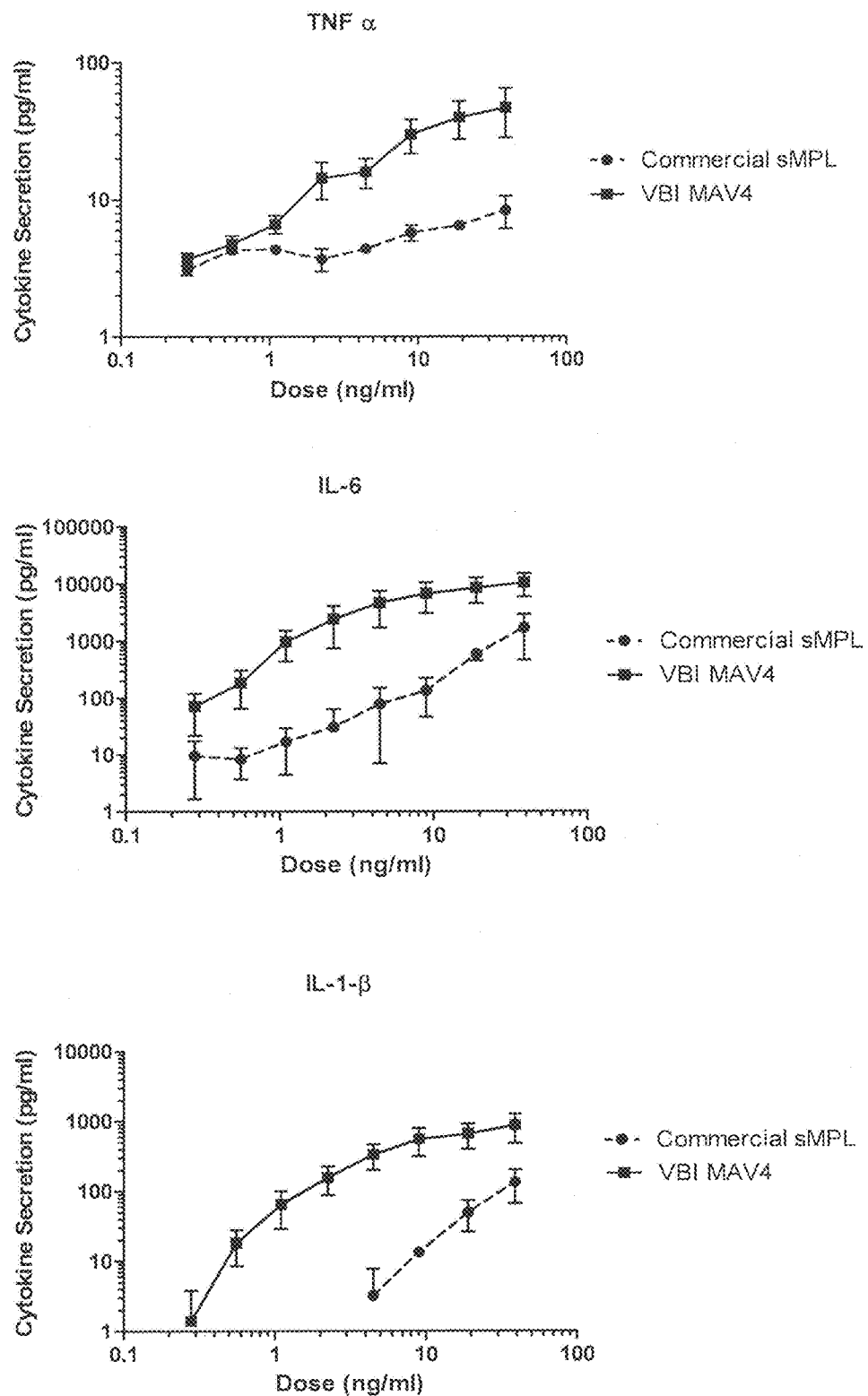
FIG. 3 shows the cytokine induction profile (A=TNF-α, B=IL-6, C=IL-1β) for phosphorylated hexaacyl disaccharide ("PHAD") and MAV4. Freshly isolated human PBMCs (n=3) were stimulated with a commercial PHAD or MAV4 and after 48 hours cytokine production was measured by CBA Assay.

FIG. 3 shows a cytokine induction profile for PHAD and MAV4 (TNF-α, IL-6 and IL-1β). Freshly isolated human PBMCs (n=3) were stimulated with a commercial PHAD or MAV4 and after 48 hours cytokine production was measured by CBA Assay as described above. An in vitro measure of adjuvant effects is the ability to elicit in a host at least one immune response that is selected from (a) production of one or a plurality of cytokines wherein the cytokine is selected from interferon-gamma (IFN-γ) or tumor necrosis factor-alpha (TNF-α); and (b) production of one or a plurality of interleukins wherein the interleukin is selected from IL-1β, IL-2, IL-3, IL-4, IL-6, IL-8, IL-10, IL-12, IL-13, IL-16, IL-18 and IL-23.

Both PHAD and MAV4 induced dose-dependent immune responses in human whole blood cells characterized by the secretion of TNF-α, IL-1β and IL-6. For all three cytokines the adjuvant MAV4 had a comparable potency to PHAD at an approximately 10-fold lower concentrations (see FIG. 3 which compares cytokine secretion for 1 ng/ml MAV4 to concentration of PHAD required to achieve comparable level of cytokine secretion).

Example 3: Reverse Phase HPLC Analysis of MPL Derivative

Reverse phase HPLC analysis of PHAD and MAV4 co-melted with 1-monopalmitoyl glycerol at the inverted melt method temperature (Example 4) was used to evaluate the thermostability or thermolability of the two adjuvants under these thermal conditions. In the procedure, the samples were prepared as follows, in isopropanol (IPA) using 1.5 ml autoinjection vials as duplicates: PHAD: 20 µg PHAD+180 µg 1-monopalmitoyl glycerol (1:9 wt ratio); MAV4: 10 µg+90 µg 1-monopalmitoyl glycerol (1:9 wt ratio).

Figure 4A:
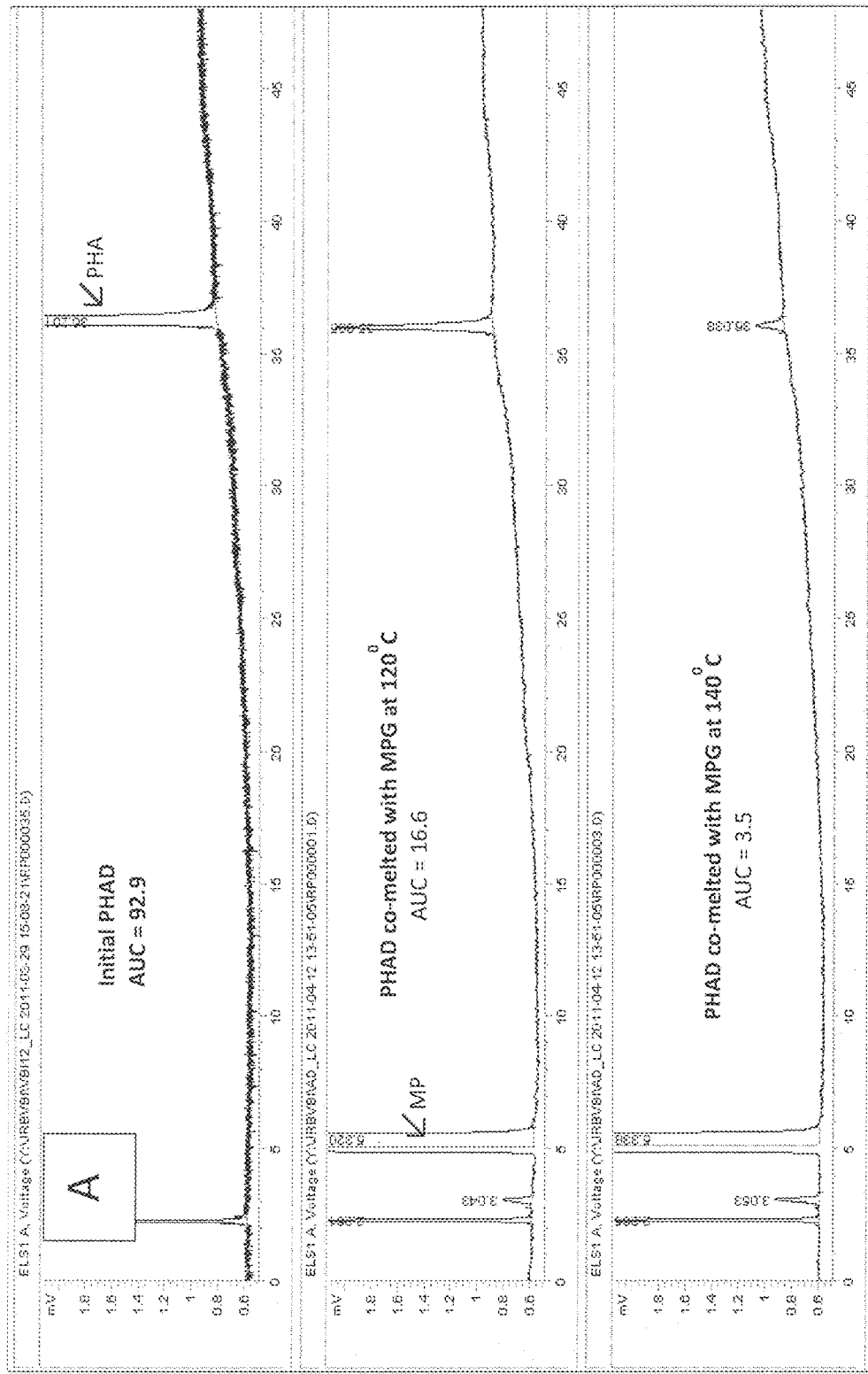
FIGS. 4A and 4B shows reverse phase HPLC analysis of PHAD (A) and MAV4 (B) co-melted with MPG at the inverted melt method temperature to evaluate the thermostability or thermolability of the two adjuvants at those thermal conditions.
Figure 4B:
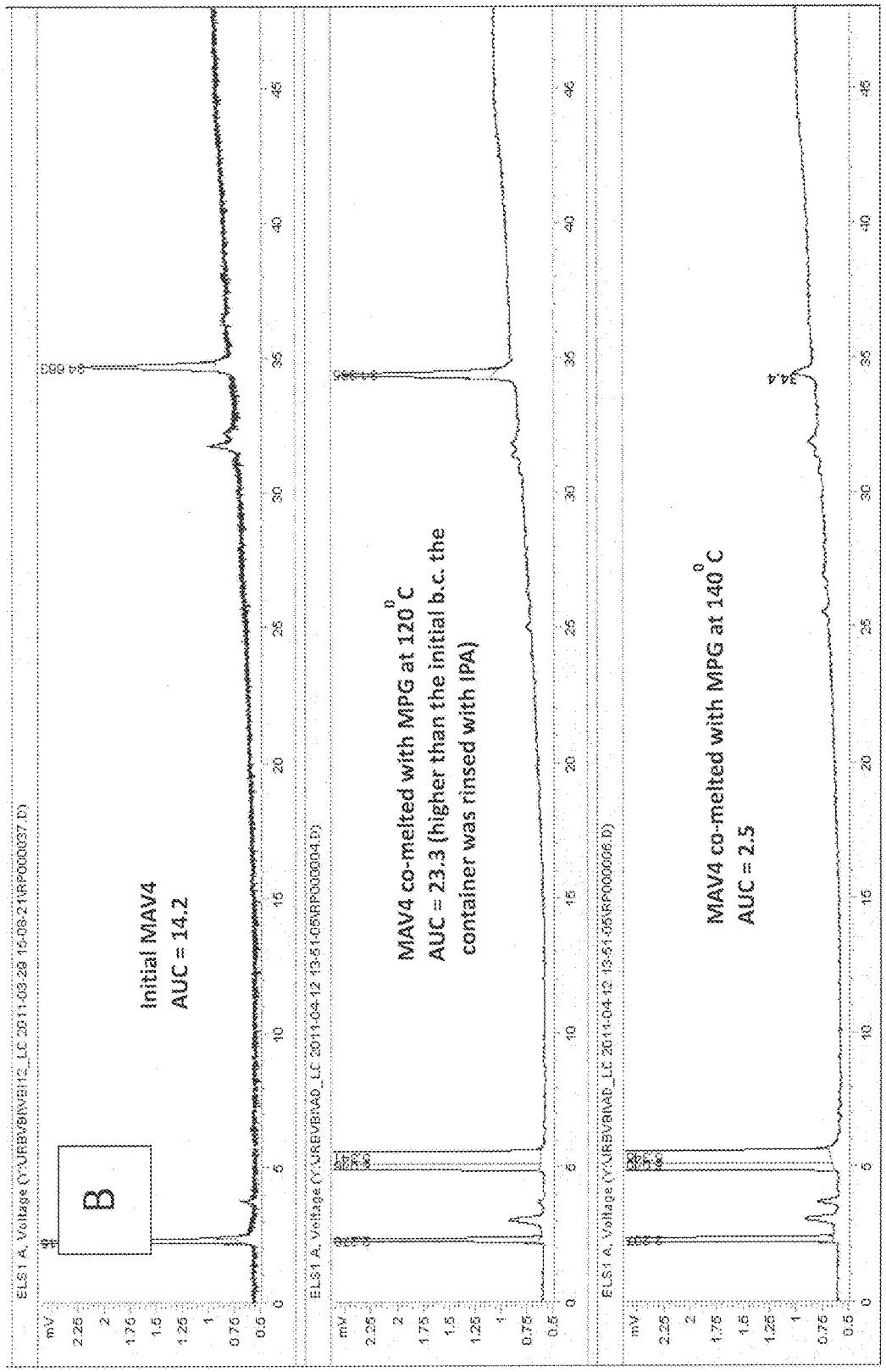
Figure 5:
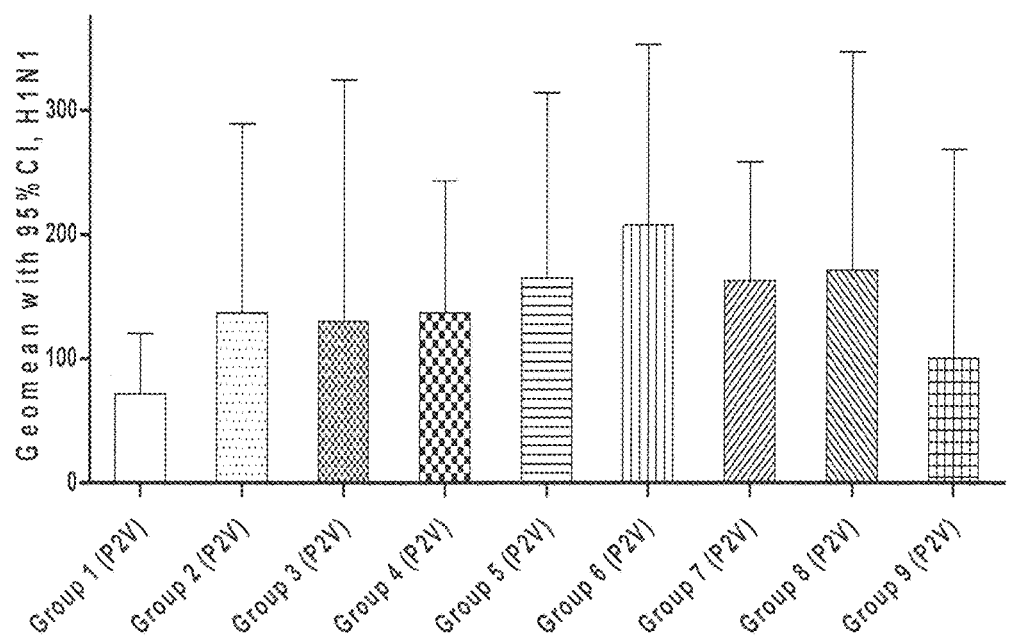
FIG. 5 shows the potency against H1N1 virus of an exemplary licensed influenza vaccine in mice (dose-sparing at $\frac{1}{30}\times$ human dose; mice receive $\frac{1}{10}^{th}$ of the human dose) either formulated into NISV or not formulated into NISV with the exemplary TLR-4 agonist adjuvants PHAD or MAV4 compared to the influenza vaccine formulated into NISV without adjuvant as described in Example 4, Table 2.

The samples were lyophilized overnight. The dried samples were melted for six minutes at 120° C. and 140° C. Each sample was then dissolved in IPA to give a concentration of 0.1 µg/µl for an HPLC load of 20 µL. A Zorbax-SBC18 column (250×4.6 mm) was used with a mobile phase A (95% Methanol-5% $H_2O$-0.1% trifluoroacetic acid (TFA) and a mobile phase B (IPA-0.1% TFA). In FIGS. 4A and 4B a significant decrease was observed in the Area Under the Curve (AUC) when the lipid and adjuvant (respectively PHAD or MAV4) was melted at a temperature of 140° C. versus 120° C. This observation could be an indication of degradation of the sample or that after melting the sample is adsorbed as a thin film on the glassware and becomes difficult to solubilize for subsequent HPLC analysis. No minor peaks were observed in the chromatogram which would suggest that degradation had not occurred.

Example 4: Preparation of Immunogenic Compositions with MPL Derivative

This Example describes methods for preparing exemplary lyophilized immunogenic compositions for intramuscular (IM) injection as described in the following Table 2.

TABLE 2

| Formulation | Fluzone ® ($^{10}/_{11}$)[1] | Antigen (µg)[3] | Adjuvant Type | Adjuvant Content (µg)[3] | Formulation Type |
|---|---|---|---|---|---|
| 1 | ⅓X human dose (⅓₀X dose)[2] | 1.5 | None | N/A | Inverted Melt NISV |
| 2 | ⅓X human dose (⅓₀X dose) | 1.5 | PHAD | 1.66 | lyophilized with sucrose and adjuvant |
| 3 | ⅓X human dose (⅓₀X dose) | 1.5 | MAV4 | 1.66 | lyophilized with sucrose and adjuvant |
| 4 | ⅓X human dose (⅓₀X dose) | 1.5 | PHAD | 1.66 | Inverted Melt NISV; lyophilized with sucrose and adjuvant |
| 5 | ⅓X human dose (⅓₀X dose) | 1.5 | MAV4 | 1.66 | Inverted Melt NISV; lyophilized with sucrose and adjuvant |
| 6 | ⅓X human dose (⅓₀X dose) | 1.5 | PHAD | 1.10[4] | Inverted Melt NISV; adjuvant co-melted |
| 7 | ⅓X human dose (⅓₀X dose) | 1.5 | MAV4 | 1.10[4] | Inverted Melt NISV; adjuvant co-melted |
| 8 | ⅓X human dose (⅓₀X dose) | 1.5 | PHAD | 1.66 | Commercial Fluzone ®; adjuvant added in aqueous solution |
| 9 | ⅓X human dose (⅓₀X dose) | 1.5 | MAV4 | 1.66 | Commercial Fluzone ®; adjuvant added in aqueous solution |

[1]Fluzone ® (2010-2011 season; Sanofi Pasteur) is an inactivated trivalent split influenza vaccine. Each 0.5 ml unit dose of Fluzone ® (2010-2011 season; Sanofi Pasteur) contains 15 µg hemagglutinin (HA) antigen from each of the following influenza virus strains: H1N1, A/California/07/2009 X-179A; H3N2, A/Victoria/210/2009 X-187 (an A/Perth/16/2009 - like virus); and B/Brisbane/60/2008.
[2]Mice receive $^{1}/_{10}^{th}$ the human dose of Fluzone ®.
[3]Content per 0.05 ml mouse dose.
[4]Adjuvant amount calculated based on 40% lipid loss that occurs during the transfer of melted lipids into the antigen solution using the inverted melt method.

A 5.29 M Phosphate buffer (pH 7.2) solution was prepared with 4.62 grams of $Na_2HPO_4$ and 19.4 grams of $NaH_2PO_4$ dissolved in 20 mL of Water for Injection (WFI). The pH of the resulting solution was adjusted to pH 7.2 and then the solution was filtered through a 0.2 micrometer Millipore 25 mm GV sterile filter. 100 ml of a 10 mM phosphate buffer (pH 7.2) was prepared by diluting 0.2 ml of 5.29 M Phosphate buffer with 99.8 ml WFI; the pH was adjusted to pH 7.2 and the solution was filtered through a 0.2 micrometer Millipore 25 mm GV sterile filter. A 400 mM sucrose solution was prepared by dissolving 68.46 grams of sucrose in 500 ml WFI and the solution was filtered through a 0.2 µm sterile filter in a laminar flow hood. A sucrose-PHAD solution was prepared by adding 400 mM sucrose solution to the exemplary adjuvant PHAD (to give a final concentration of 100 µg/ml); the solution was then sonicated and heated at 60-70° C. until total dissolution occurred and cooled to 30-35° C. prior to use. A sucrose-MAV4 solution was prepared by adding 400 mM sucrose solution to the exemplary adjuvant MAV4 (to give a final concentration of 100 µg/ml); the solution was then sonicated and heated at 60-70° C. until total dissolution occurred and cooled to 30-35° C. prior to use. A buffer-PHAD solution was prepared by adding 10 mM Phosphate Buffer (pH 7.2) to the exemplary adjuvant PHAD (to give a final concentration of 50 µg/ml); the solution was then sonicated and heated for at 60-70° C. until total dissolution occurred and cooled to 30-35° C. prior to use. A buffer-MAV4 solution was prepared by adding 10 mM Phosphate Buffer (pH 7.2) to the exemplary adjuvant MAV4 (to give a final concentration of 50 µg/ml); the solution was then sonicated and heated at 60-70° C. until total dissolution occurred and cooled to 30-35° C. prior to use.

Test articles 1, 4 and 5 in Table 2 were all non-ionic surfactant vesicle (NISV) formulations and were prepared by the inverted melt method. The NISVs were composed of the following lipids: 1-monopalmitoyl glycerol (a non-ionic surfactant), cholesterol (a steroid) and dicetyl phosphate (an ionic surfactant). Specifically, a 5:4:1 molar ratio of lipids (200.2 mg of 1-monopalmitoyl glycerol (MPG), 188.1 mg of cholesterol (CHO), and 66 mg of dicetyl phosphate (DCP)) was placed in a flat bottom glass beaker, ensuring none of the powder adhered to the side of the glass beaker. The beaker was clamped and covered with aluminum foil and the lipids were melted in a heated oil bath at 120-125° C. with occasional swirling in the beaker. While the lipids were melting, 300 µl of 5.29M Phosphate buffer (pH 7.2) was added to 15 ml of Fluzone® influenza vaccine (2010-2011 season; Sanofi Pasteur) in a laminar flow hood. Fluzone® influenza vaccine (2010-2011 season; Sanofi Pasteur) is an inactivated trivalent split influenza vaccine which contains influenza hemagglutinin (HA) antigen at a concentration of 45 µg/0.5 ml (each 0.5 ml contains 15 µg HA antigen from each of the following influenza virus strains: H1N1, A/California/07/2009 X-179A; H3N2, A/Victoria/210/2009 X-187 (an A/Perth/16/2009-like virus); and B/Brisbane/60/2008). The buffered antigen stock solution was pre-incubated at 30-35° C. for 5-8 minutes, and then homogenized (at 8,000 rpm) at 30-35° C., and quickly (to prevent crystallization) the melted lipids were transferred into the beaker while homogenizing the solution, at which point homogenization at 8,000 rpm continued for 10 minutes at 30-35° C. The resulting lipid-antigen suspension was shaken for 1-2 hours at 220±10 rpm at 30-35° C.

For test article 1, without adjuvant, 8 ml of the lipid-antigen suspension was diluted with 8 ml of 400 mM sucrose solution in water. For test article 4, with exemplary adjuvant PHAD, 3 ml of the lipid-antigen suspension was diluted with 3 ml of the Sucrose-PHAD solution (100 µg/ml). For test article 5, with exemplary adjuvant MAV4, 3 ml of the lipid-antigen suspension was diluted with 3 ml of the Sucrose-MAV4 solution (100 µg/ml). The NISVs were then aliquoted into sterile vials (334 µl/vial), sealed with a sterile rubber stopper and frozen at −80° C. for at least 8 hours and subsequently lyophilized.

For test articles 2 and 3 formulated without NISVs and containing antigen and adjuvant only, either 3 ml of the Sucrose-PHAD solution (100 µg/ml) or 3 ml of the Sucrose-MAV4 solution (100 µg/ml) was added to 3 ml of Fluzone vaccine and the subsequent solution was shaken in an incubator/shaker for 35 minutes at 220±10 rpm at 30-35° C. The solutions were aliquoted into sterile vials (334 µl/vial), sealed with a sterile rubber stopper and frozen at −80° C. for at least 8 hours and subsequently lyophilized.

Test articles 6 and 7 in Table 2 were non-ionic surfactant vesicle (NISV) formulations and were prepared by the inverted melt method. The NISVs were composed of the following lipids: 1-monopalmitoyl glycerol (a non-ionic surfactant), cholesterol (a steroid) and dicetyl phosphate (an ionic amphiphile). Specifically, a 5:4:1 molar ratio of lipids (67.1 mg of 1-monopalmitoyl glycerol (MPG), 62.7 mg of cholesterol (CHO), and 22 mg of dicetyl phosphate (DCP)) was placed in a flat bottom glass beaker, ensuring none of the powder adhered to the side of the glass beaker. The exemplary adjuvant PHAD or the exemplary adjuvant MAV4 were co-melted with the lipids. The beaker was clamped and covered with aluminum foil and the lipids were melted in a heated oil bath at 120-125° C. with occasional swirling in the beaker. While the lipids and adjuvants were melting, 100 µl of 5.29M phosphate buffer (pH 7.2) was added to 5 ml of Fluzone® influenza vaccine (2010-2011 season; Sanofi Pasteur) in a laminar flow hood. The buffered antigen stock solution was pre-incubated at 30-35° C. for 5-8 minutes, and then homogenized (at 8,000 rpm) at 30-35° C., and quickly (to prevent crystallization) the melted lipids and adjuvants were transferred into the beaker while homogenizing the solution, at which point homogenization at 8,000 rpm continued for 10 minutes at 30-35° C. The resulting lipid-antigen-adjuvant suspension was shaken for 1-2 hours at 220±10 rpm at 30-35° C. An equal volume (5 ml) of 400 mM sucrose solution was added to each lipid-antigen-adjuvant suspension. The NISVs were then aliquoted into sterile vials (334 µl/vial), sealed with sterile rubber stoppers and frozen at −80° C. for at least 8 hours and subsequently lyophilized.

For test articles 8 and 9 formulated without NISVs and containing antigen and adjuvant only, either 6 ml of the buffer-PHAD solution (50 µg/ml) or 6 ml of the Buffer-MAV4 solution (50 µg/ml) were added to 3 ml of Fluzone vaccine and the subsequent solutions were shaken in an incubator/shaker for 35 minutes at 220±10 rpm at 30-35° C. The solutions were then aliquoted into sterile vials (500 µl/vial), sealed with a sterile rubber stoppers and stored at 2-8° C. until analysis or administration.

All lyophilized NISVs formulations and lyophilized unformulated antigen-adjuvant solutions were rehydrated prior to administration in 0.5 ml of WFI.

Example 5: Sandwich ELISA of Hemagglutinin Content of Immunogenic Compositions

For in vitro potency testing, the sandwich ELISA (sELISA) assay was used to measure Hemagglutinin (HA) antigen content in immunogenic compositions. Aliquots of reconstituted samples were centrifuged in an ultracentrifuge at 24,000 rpm, for 10 minutes at 4° C. and supernatant and pellet fractions were removed, extracted and analyzed by sELISA to determine antigen content. 96-well ELISA plates were coated overnight at 4° C. with a coating solution of capture antibody, anti-A/California/07/2009 H1N1 HA serum diluted 1/500 in carbonate-bicarbonate buffer, pH 9.7. Next morning the coating solution was removed from the plates and then a blocking solution was added and the plates were blocked (1-3 hours at 37° C.) with 5% fetal bovine serum (FBS) in ELISA wash buffer (EWB 0.05% Tween 20 in PBS). After the incubation time, plates were washed with wash buffer (0.05% Tween 20 in PBS). The starting dilution of the samples and standards (in 5% FBS in PBS were prepared and seven 2-fold serial dilutions were subsequently prepared. The samples and the standards (Fluzone® vaccine 2010-2011) were added to the 96-well ELISA plates and were incubated for 1.5 hours at 37° C. The plates were washed six times in wash buffer and incubated for 1.0 hours at 37° C. with a 1/500 dilution of either a rabbit polyclonal or monoclonal antibody to influenza H1N1 HA as a primary antibody. The plates were washed six times in wash buffer and incubated for 1.0 hour at 37° C. with a 1/10000 dilution of a goat anti-rabbit IgG-Fc HRP (Horse Radish Peroxidase) conjugated secondary antibody (Bethyl). Alternatively, a rabbit polyclonal antibody to influenza H1N1 HA directly conjugated to HRP was also used as a primary antibody eliminating the need for a HRP conjugated secondary antibody step. The plates were washed six times and developed with 100 µl of TMB substrate for 8 min. 100 µl of TMB-Stop solution was added to stop the reaction. Absorbance was read at 450 nm with an ELISA plate reader (Bio-Rad). The $OD_{450}$ readings were determined and the results (raw data) were analyzed using the plate reader software (soft Max). The values of the standard curve were used to calculate the concentration of each sample. The linear part of the standard curve was between 0.1-7.5 ng/ml for each influenza strain related protein. For each sample, the dilution giving a concentration in the range of the linear part of the standard curve was used to calculate the original sample concentration.

Table 3 shows antigen association (pellet) and total antigen recovery, for the various formulations, as determined by sELISA with either monoclonal or polyclonal antibodies. Antigenicity, evaluated as total antigen recovery (from the two fractions, pellet and supernatant), ranged from 73% to 108% using the monoclonal antibody and from 62% to 99% using the polyclonal antibodies. Antigen association was observed in all NISVs formulated test articles in the range of 31% to 57%, irrespective of the type of antibody used (monoclonal or polyclonal). The presence of different adjuvants did not affect the antigen recovery or association, and no significant differences were found when comparing formulations containing adjuvants, PHAD or MAV4, versus the control formulation without adjuvant.

TABLE 3

| TA | Ag % Recovery by Rabbit Monoclonal to H1N1 (RM02) | | | Ag % Recovery by Rabbit Polyclonal to H1N1 | | | Ag % Recovery by Rabbit Polyclonal HRP conjugated | | |
|---|---|---|---|---|---|---|---|---|---|
| | Pellet | Supernatant | Total | Pellet | Supernatant | Total | Pellet | Supernatant | Total |
| 1 | 53 | 27 | 80 | 36 | 34 | 70 | 36 | 27 | 63 |
| 2 | 7 | 83 | 90 | 5 | 77 | 82 | 11 | 88 | 99 |
| 3 | 6 | 95 | 101 | 4 | 58 | 62 | 8 | 69 | 77 |
| 4 | 57 | 42 | 99 | 37 | 32 | 69 | 44 | 42 | 86 |
| 5 | 53 | 55 | 108 | 37 | 32 | 69 | 41 | 27 | 68 |
| 6 | 36 | 54 | 90 | 31 | 48 | 79 | 34 | 48 | 82 |
| 7 | 43 | 45 | 88 | 39 | 52 | 91 | 41 | 57 | 98 |
| 8 | 6 | 67 | 73 | 6 | 82 | 88 | 6 | 82 | 88 |
| 9 | 6 | 73 | 79 | 7 | 85 | 92 | 7 | 92 | 99 |

Example 6: Hemagglutinin Inhibition Assay of Potency of Immunogenic Compositions For in vivo potency testing, the Hemagglutinin Inhibition Assay (HAI) assay was used to measure immunological responses in animals. The HAI assay is a serological technique used to detect HA antibody in serum resulting from infection or vaccination with influenza virus, and HAI titres correlate with protection from influenza in humans. The HAI antibody titre is expressed as the reciprocal of the highest serum dilution showing complete hemmaglutination using four hemagglutination units. An HAI titre of 1:40 or higher is considered as seroprotective, and a four-fold increase in HAI titres in samples taken after and before vaccination is the minimum increase considered necessary for classification of seroconversion. Results are presented as the inverse of HAI titre and geometric mean HAI titre.

The HAI assay is performed as follows. Briefly, a series of 2-fold dilutions in PBS of sera from immunized mice were prepared in 96-well V-bottomed plates and incubated at room temperature for 30 min with 50 μl of four hemmaglutinating units (HAU) of A/California/07/2009 (H1N1) or A/Perth/16/2009 (H3N2). Next, 50 μl of chicken red blood cells (diluted 0.5% v/v) (Canadian Food Inspection Agency, Ottawa, Canada) was added to all wells on the plate and incubated for 1.5 h at room temperature. The highest dilution capable of agglutinating chicken red blood cells was then determined.

Geometric means, median and standard error of the mean were determined. Statistical analysis was carried out using the Software GraphPad Prism 5. Paired samples were assessed by paired-t test and non-paired samples by student t-test. The P values ≤0.05 were considered to be statistically significant. A positive response was indicated by ≥two-fold increase of 14 day post vaccination responses after the last vaccine dose compared to the values obtained before immunization. The results of these assays are described below.

Example 7: Influenza Immunization of Mice with Immunogenic Compositions

Various adjuvanted (PHAD and MAV4) dose-sparing formulations (with and without NISVs), prepared as described in Example 4 were tested in female BALB/C mice 6-8 weeks old (minimum 8 animals per test group) with commercial Fluzone® formulated in NISVs and unadjuvanted acting as a positive control. The mice were immunized intramuscularly with 50 μl of the rehydrated formulations twice, once on day 0 and once on day 14. Blood was collected from all mice in the study groups pre-immunization and then post-$1^{st}$ and -$2^{nd}$ immunizations to assess humoral immune responses. Animals received either the unadjuvanted Fluzone® at the equivalent of a 1/30× human dose formulated in NISV (dose-sparing Fluzone® 1/3× human dose; mice receive $1/10^{th}$ human dose (Group 1) or with the adjuvant PHAD or the adjuvant MAV4 either added prior to lyophilization (Groups 4 and 5) or co-melted with other lipids (Groups 6 and 7). The adjuvants were also admixed with unformulated Fluzone® at the equivalent of a 1/30× human dose (dose-sparing Fluzone® 1/3× human dose; mice receive $1/10^{th}$ human dose) and either lyophilized (Groups 2 and 3) or left in an aqueous buffer (Groups 8 and 9). The various test formulations are described in detail in Table 2.

FIG. 5 shows the potency against H1N1 virus of an exemplary licensed influenza vaccine in mice (dose-sparing at 1/30× human dose; mice receive $1/10^{th}$ of the human dose) either formulated into NISV or not formulated into NISV with the exemplary TLR-4 agonist adjuvants PHAD or MAV4 compared to the influenza vaccine formulated into NISV without adjuvant as described in Example 4, Table 2. It can be seen that the mean for HAI titre against H1N1 for all of the adjuvanted groups (Groups 2-9) were higher than for group 1 treated with formulated unadjuvanted Fluzone® vaccine. When consideration is given to the fact that the adjuvant concentration in the co-melted formulations is 40% less than in the admixed formulations due to lipid loss that occurs during the process of transferring the melted lipids to the aqueous Fluzone® vaccine, it can be seen that the mean for HAI titre against H1N1 for the adjuvanted groups (Groups 6 and 7) where the adjuvant was co-melted with the vesicle-forming lipids was higher than for the other groups (Groups 4 and 5) with the same adjuvants but where the adjuvant was admixed with the NISVs prior to lyophilization.

Figure 6:
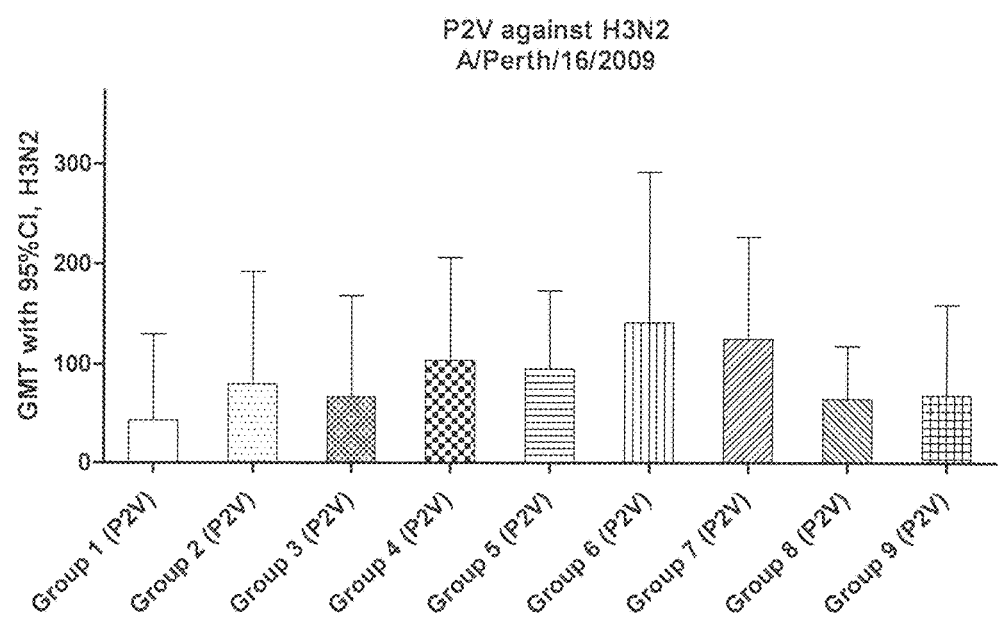
FIG. 6 shows the potency against H3N2 virus of an exemplary licensed influenza vaccine in mice (dose-sparing at $\frac{1}{30}\times$ human dose; mice receive $\frac{1}{10}^{th}$ of the human dose) either formulated into NISV or not formulated into NISV with the exemplary TLR-4 agonist adjuvants PHAD or MAV4 compared to the influenza vaccine formulated into NISV without adjuvant as described in Example 4, Table 2.

FIG. 6 shows the potency against H3N2 virus of an exemplary licensed influenza vaccine in mice (dose-sparing at ⅓₀× human dose; mice receive ⅟₁₀$^{th}$ of the human dose) either formulated into NISV or not formulated into NISV with the exemplary TLR-4 agonist adjuvants PHAD or MAV4 compared to the influenza vaccine formulated into NISV without adjuvant as described in Example 4, Table 2. It can be seen that the mean for HAI titre against H1N1 for all of the adjuvanted groups (Groups 2-9) were higher than for group 1 treated with formulated unadjuvanted Fluzone® vaccine. When consideration is given to the fact that the adjuvant concentration in the co-melted formulations is 40% less than in the admixed formulations due to lipid loss that occurs during the process of transferring the melted lipids to the aqueous Fluzone® vaccine, it can be seen that the mean for HAI titre against H1N1 for the adjuvanted groups (Groups 6 and 7) where the adjuvant was co-melted with the vesicle-forming lipids was higher than for the other groups (Groups 4 and 5) with the same adjuvants but where the adjuvant was admixed with the NISVs prior to lyophilization.

Example 8: Influenza Immunization of Monkey with Immunogenic Compositions

To examine immunogenicity in a non-human primate model, the formulations are also tested in rhesus macaques. Monkeys receive two injections (0, 28 days) of either (a) commercial Fluzone® vaccine control (1× human dose of 45 μg) or (b) a dose-sparing (⅓× human dose of 15 μg) amount of Fluzone® formulated in NISV with and without the exemplary TLR-4 agonist PHAD (50 μg) or MAV4 (50 μg). Serum samples are collected pre- and post-IM injection (for up to 10 weeks post 2$^{nd}$ injection) and analyzed by HAI assay for H1N1 and H3N2 as described in Example 6.

INCORPORATION BY REFERENCE

The contents of any reference that is referred to herein are hereby incorporated by reference in their entirety.

Other Embodiments

It is intended that the specification and examples be considered as exemplary only. Other embodiments will be apparent to those skilled in the art from a consideration of the specification or practice of the compounds, compositions and methods disclosed herein.

What is claimed is:

1. A composition comprising:
   (i) a non-ionic surfactant vesicle comprising: 1-monopalmitoyl glycerol, dicetyl phosphate, and cholesterol; and an immunostimulatory amount of a compound of formula I which is co-melted with the non-ionic surfactant vesicle, wherein:
   $R^1$, $R^2$, $R^3$, $R^4$, $R^5$, and $R^6$ are $C_x$ alkyl; x is an integer from 6 to 11; and
   $R^1$, $R^2$, $R^3$, $R^4$, $R^5$, and $R^6$ are the same; and
   (ii) an antigen.

2. The composition of claim 1, wherein x is 6.

3. The composition of claim 1, wherein x is 8.

4. The composition of claim 1, wherein x is 11.

5. The composition of claim 1, wherein $R^1$, $R^2$, $R^3$, $R^4$, $R^5$, and $R^6$ are unbranched.

6. The composition of claim 1, wherein the antigen is a virus selected from the group consisting of an attenuated virus, an inactivated virus, a whole virus and a split virus.

7. The composition of claim 6, wherein the virus is hepatitis A or influenza.

8. The composition of claim 1, wherein the antigen is a bacteria selected from the group consisting of *Bordetella pertussis*, *Vibrio cholerae* and *Salmonella typhi*.

9. The composition of claim 1, wherein the antigen is a polypeptide.

10. The composition of claim 9, wherein the polypeptide is a viral polypeptide.

11. The composition of claim 10, wherein the viral polypeptide is selected from the group consisting of a hepatitis A polypeptide, a hepatitis B polypeptide, HBsAg, a hepatitis C polypeptide, an HIV polypeptide and an influenza polypeptide.

12. The composition of claim 9, wherein the polypeptide is hemagglutinin, neuraminidase, or a combination thereof.

13. The composition of claim 1, wherein the composition comprises a mixture of antigens.

14. The composition of claim 1, wherein the composition comprises a mixture of polypeptides.

15. The composition of claim 1, wherein the antigen is a polynucleotide.

16. The composition of claim 1, wherein the antigen is a polysaccharide.

17. The composition of claim 1, wherein the antigen is a viral-like particle.

18. A method comprising administering to a patient in need thereof a therapeutically effective amount of the composition of claim 1.

19. The method of claim 18, wherein the composition is administered by intramuscular injection.

* * * * *